US012557977B2

(12) United States Patent
Farkash et al.

(10) Patent No.: US 12,557,977 B2
(45) Date of Patent: Feb. 24, 2026

(54) SMARTPHONE DENTAL IMAGING ATTACHMENT APPARATUS

(71) Applicant: Align Technology, Inc., San Jose, CA (US)

(72) Inventors: Shai Farkash, Hod HaSharon (IL); Yossef Y. Atiya, Modin-maccabim-Reut (IL); Maayan Moshe, Ramat HaSharon (IL)

(73) Assignee: Align Technology, Inc., San Jose, CA (US)

( * ) Notice: Subject to any disclaimer, the term of this patent is extended or adjusted under 35 U.S.C. 154(b) by 579 days.

(21) Appl. No.: 17/730,136

(22) Filed: Apr. 26, 2022

(65) Prior Publication Data

US 2022/0338723 A1 Oct. 27, 2022

Related U.S. Application Data

(63) Continuation-in-part of application No. 29/827,196, filed on Feb. 17, 2022, now Pat. No. Des. 1,027,186, and a continuation-in-part of application No. 29/780,745, filed on Apr. 26, 2021, now Pat. No. Des. 1,063,077.

(60) Provisional application No. 63/212,583, filed on Jun. 18, 2021, provisional application No. 63/180,008, filed on Apr. 26, 2021.

(51) Int. Cl.
*A61B 1/24* (2006.01)
*A61B 1/05* (2006.01)

(52) U.S. Cl.
CPC ................ *A61B 1/24* (2013.01); *A61B 1/053* (2013.01); *A61B 2560/0406* (2013.01); *A61B 2560/0443* (2013.01)

(58) Field of Classification Search
CPC ................................. A61B 1/24; A61B 5/682
See application file for complete search history.

(56) References Cited

U.S. PATENT DOCUMENTS

| | | | |
|---|---|---|---|
| 3,971,954 A | 7/1976 | Kleinberg et al. | |
| D368,523 S | 4/1996 | Mendoza | |
| D371,199 S | 6/1996 | Mendoza | |
| (Continued) | | | |

FOREIGN PATENT DOCUMENTS

| | | | |
|---|---|---|---|
| EP | 3297517 B1 | 2/2021 | |
| GB | 6224549 A | 9/2022 | |
| (Continued) | | | |

OTHER PUBLICATIONS

Dental Camera Scan Box Pro; Dental Monitoring; Medical Expo; 5 pages; retrieved from the internet (https://www.medicalexpo.com/prod/dental-monitoring/product-4579092-1108503.html) on Jul. 29, 2025.

(Continued)

*Primary Examiner* — Julianna N Harvey
(74) *Attorney, Agent, or Firm* — Shay Glenn LLP

(57) ABSTRACT

Provided herein are systems for monitoring a subject's teeth during orthodontic treatment. In particular, described herein are apparatuses having a fixed focal length for coupling to a patient's smartphone, including a built-in lip/cheek retractor. These smartphone dental imaging apparatuses may be configured to easily and robustly interface with the user's smartphone to allow capture of dental images.

23 Claims, 26 Drawing Sheets

(56)                    References Cited

U.S. PATENT DOCUMENTS

| | | | |
|---|---|---|---|
| D372,088 S | 7/1996 | Frush |
| 6,099,314 A | 8/2000 | Kopelman et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |
| 6,334,772 B1 | 1/2002 | Taub et al. |
| 6,334,853 B1 | 1/2002 | Kopelman et al. |
| 6,371,761 B1 | 4/2002 | Cheang et al. |
| 6,386,878 B1 | 5/2002 | Pavlovskaia et al. |
| 6,409,504 B1 | 6/2002 | Jones et al. |
| 6,457,972 B1 | 10/2002 | Chishti et al. |
| 6,463,344 B1 | 10/2002 | Pavloskaia et al. |
| 6,488,499 B1 | 12/2002 | Miller |
| 6,514,074 B1 | 2/2003 | Chishti et al. |
| 6,542,249 B1 | 4/2003 | Kofman et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,633,789 B1 | 10/2003 | Nikolskiy et al. |
| 6,664,986 B1 | 12/2003 | Kopelman et al. |
| 6,688,886 B2 | 2/2004 | Hughes et al. |
| 6,697,164 B1 | 2/2004 | Babayoff et al. |
| 6,726,478 B1 | 4/2004 | Isiderio et al. |
| 6,739,869 B1 | 5/2004 | Taub et al. |
| 6,767,208 B2 | 7/2004 | Kaza |
| 6,783,360 B2 | 8/2004 | Chishti |
| 6,845,175 B2 | 1/2005 | Kopelman et al. |
| D513,322 S | 12/2005 | Jackson, III et al. |
| 6,979,196 B2 | 12/2005 | Nikolskiy et al. |
| 7,001,270 B2 | 2/2006 | Taub |
| 7,030,383 B2 | 4/2006 | Babayoff et al. |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,202,466 B2 | 4/2007 | Babayoff et al. |
| 7,241,142 B2 | 7/2007 | Abolfathi et al. |
| 7,255,558 B2 | 8/2007 | Babayoff et al. |
| D553,980 S | 10/2007 | Verweyst et al. |
| 7,286,954 B2 | 10/2007 | Kopelman et al. |
| 7,293,988 B2 | 11/2007 | Wen |
| 7,309,230 B2 | 12/2007 | Wen |
| 7,319,529 B2 | 1/2008 | Babayoff |
| 7,357,634 B2 | 4/2008 | Knopp |
| 7,373,286 B2 | 5/2008 | Nikolskiy et al. |
| 7,383,198 B1 | 6/2008 | Sepe |
| 7,507,088 B2 | 3/2009 | Taub et al. |
| 7,545,372 B2 | 6/2009 | Kopelman et al. |
| 7,555,403 B2 | 6/2009 | Kopelman et al. |
| 7,580,846 B2 | 8/2009 | Chishti et al. |
| 7,637,740 B2 | 12/2009 | Knopp |
| D608,888 S | 1/2010 | Braynin et al. |
| 7,689,398 B2 | 3/2010 | Cheng et al. |
| 7,698,068 B2 | 4/2010 | Babayoff |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,870,280 B2 | 1/2011 | Kuo |
| 7,878,804 B2 | 2/2011 | Korytov et al. |
| 7,880,751 B2 | 2/2011 | Kuo et al. |
| 7,904,307 B2 | 3/2011 | Abolfathi et al. |
| 7,904,308 B2 | 3/2011 | Arnone et al. |
| 7,916,911 B2 | 3/2011 | Kaza et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 7,987,099 B2 | 7/2011 | Kuo et al. |
| 8,024,198 B2 | 9/2011 | Kuo |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,244,028 B2 | 8/2012 | Kuo et al. |
| 8,260,591 B2 | 9/2012 | Kass et al. |
| 8,275,180 B2 | 9/2012 | Kuo |
| D669,587 S | 10/2012 | Mayer |
| D678,379 S | 3/2013 | Oneill et al. |
| 8,401,826 B2 | 3/2013 | Cheng et al. |
| 8,439,672 B2 | 5/2013 | Matov et al. |
| 8,562,338 B2 | 10/2013 | Kitching et al. |
| D693,919 S | 11/2013 | Miu |
| 8,587,582 B2 | 11/2013 | Matov et al. |
| 8,591,225 B2 | 11/2013 | Wu et al. |
| D697,957 S | 1/2014 | Glasse et al. |
| 8,738,394 B2 | 5/2014 | Kuo |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 8,948,482 B2 | 2/2015 | Levin |
| D727,385 S | 4/2015 | Oneill et al. |
| 9,037,439 B2 | 5/2015 | Kuo et al. |
| 9,060,829 B2 | 6/2015 | Sterental et al. |
| 9,125,709 B2 | 9/2015 | Matty |
| D742,518 S | 11/2015 | Barak et al. |
| 9,192,305 B2 | 11/2015 | Levin |
| 9,211,166 B2 | 12/2015 | Kuo et al. |
| 9,220,580 B2 | 12/2015 | Borovinskih et al. |
| 9,261,356 B2 | 2/2016 | Lampert et al. |
| 9,261,358 B2 | 2/2016 | Atiya et al. |
| 9,299,192 B2 | 3/2016 | Kopelman |
| 9,364,296 B2 | 6/2016 | Kuo |
| 9,375,300 B2 | 6/2016 | Matov et al. |
| D760,901 S | 7/2016 | Barak et al. |
| 9,393,087 B2 | 7/2016 | Moalem |
| D763,340 S | 8/2016 | Oneill et al. |
| 9,408,679 B2 | 8/2016 | Kopelman |
| 9,414,897 B2 | 8/2016 | Wu et al. |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D770,623 S | 11/2016 | Robichaud |
| D771,817 S | 11/2016 | Barak et al. |
| 9,491,863 B2 | 11/2016 | Boltanski |
| 9,492,245 B2 | 11/2016 | Sherwood et al. |
| D774,193 S | 12/2016 | Makmel et al. |
| 9,510,757 B2 | 12/2016 | Kopelman et al. |
| 9,642,678 B2 | 5/2017 | Kuo |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,248,883 B2 | 4/2019 | Borovinskih et al. |
| D847,787 S | 5/2019 | Weirun |
| D854,694 S | 7/2019 | Wardius, Jr. et al. |
| 10,342,638 B2 | 7/2019 | Kitching et al. |
| 10,380,212 B2 | 8/2019 | Elbaz et al. |
| 10,390,913 B2 | 8/2019 | Sabina et al. |
| 10,453,269 B2 | 10/2019 | Furst |

(56) References Cited

U.S. PATENT DOCUMENTS

| | | | |
|---|---|---|---|
| 10,456,043 B2 | 10/2019 | Atiya et al. | |
| 10,463,452 B2 | 11/2019 | Matov et al. | |
| 10,467,815 B2 | 11/2019 | Marom et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,595,966 B2 | 3/2020 | Carrier, Jr. et al. | |
| 10,617,489 B2 | 4/2020 | Grove et al. | |
| 10,695,150 B2 | 6/2020 | Kopelman et al. | |
| 10,708,574 B2 | 7/2020 | Furst et al. | |
| 10,722,328 B2 | 7/2020 | Velazquez et al. | |
| D892,333 S | 8/2020 | Warlick | |
| 10,772,506 B2 | 9/2020 | Atiya et al. | |
| 10,779,718 B2 | 9/2020 | Meyer et al. | |
| 10,792,127 B2 | 10/2020 | Kopelman et al. | |
| 10,813,727 B2 | 10/2020 | Sabina et al. | |
| 10,828,130 B2 | 11/2020 | Pokotilov et al. | |
| 10,835,349 B2 | 11/2020 | Cramer et al. | |
| D906,523 S | 12/2020 | Pellissard et al. | |
| 10,885,521 B2 | 1/2021 | Miller et al. | |
| 10,888,399 B2 | 1/2021 | Kopelman et al. | |
| D909,594 S | 2/2021 | Kothari et al. | |
| 10,952,816 B2 | 3/2021 | Kopelman | |
| 10,980,612 B2 | 4/2021 | Jang | |
| 10,980,613 B2 | 4/2021 | Shanjani et al. | |
| 10,996,813 B2 | 5/2021 | Makarenkova et al. | |
| 10,997,727 B2 | 5/2021 | Xue et al. | |
| 11,013,581 B2 | 5/2021 | Sabina et al. | |
| 11,020,205 B2 | 6/2021 | Li et al. | |
| 11,020,206 B2 | 6/2021 | Shi et al. | |
| 11,026,766 B2 | 6/2021 | Chekh et al. | |
| 11,033,359 B2 | 6/2021 | Velazquez et al. | |
| D925,739 S | 7/2021 | Ariel et al. | |
| 11,071,608 B2 | 7/2021 | Derakhshan et al. | |
| 11,096,763 B2 | 8/2021 | Akopov et al. | |
| 11,096,765 B2 | 8/2021 | Atiya et al. | |
| 11,116,605 B2 | 9/2021 | Nyukhtikov et al. | |
| 11,147,652 B2 | 10/2021 | Mason et al. | |
| 11,151,753 B2 | 10/2021 | Gao et al. | |
| 11,238,586 B2 | 2/2022 | Minchenkov et al. | |
| 11,367,192 B2 | 6/2022 | Kopelman et al. | |
| D958,370 S | 7/2022 | Mirelez, Jr. et al. | |
| D962,437 S * | 8/2022 | Oren-Artzi | D24/152 |
| D971,407 S | 11/2022 | Liu et al. | |
| D971,408 S | 11/2022 | Liu et al. | |
| D982,752 S * | 4/2023 | Pellissard | D24/152 |
| D988,514 S | 6/2023 | Oren-Artzi et al. | |
| D989,312 S | 6/2023 | Frenkler et al. | |
| RE49,605 E | 8/2023 | Kopelman | |
| D1,027,186 S | 5/2024 | Farkash et al. | |
| D1,063,077 S | 2/2025 | Farkash et al. | |
| 2002/0188478 A1 | 12/2002 | Breeland et al. | |
| 2003/0143509 A1 | 7/2003 | Kopelman et al. | |
| 2003/0148243 A1 | 8/2003 | Kerschbaumer et al. | |
| 2003/0207227 A1 | 11/2003 | Abolfathi | |
| 2004/0152036 A1 | 8/2004 | Abolfathi | |
| 2004/0186390 A1 * | 9/2004 | Ross | A61B 5/083 600/532 |
| 2004/0197728 A1 | 10/2004 | Abolfathi et al. | |
| 2004/0259049 A1 | 12/2004 | Kopelman et al. | |
| 2005/0159986 A1 | 7/2005 | Breeland et al. | |
| 2005/0182654 A1 | 8/2005 | Abolfathi et al. | |
| 2005/0244791 A1 | 11/2005 | Davis et al. | |
| 2006/0127836 A1 | 6/2006 | Wen | |
| 2006/0127852 A1 | 6/2006 | Wen | |
| 2006/0127854 A1 | 6/2006 | Wen | |
| 2006/0275731 A1 | 12/2006 | Wen et al. | |
| 2006/0275736 A1 | 12/2006 | Wen et al. | |
| 2008/0288289 A1 | 11/2008 | Sah | |
| 2008/0306724 A1 | 12/2008 | Kitching et al. | |
| 2010/0009308 A1 | 1/2010 | Wen et al. | |
| 2010/0068672 A1 | 3/2010 | Arjomand et al. | |
| 2010/0068676 A1 | 3/2010 | Mason et al. | |

| | | | |
|---|---|---|---|
| 2010/0092907 A1 | 4/2010 | Knopp | |
| 2010/0167243 A1 | 7/2010 | Spiridonov et al. | |
| 2013/0204599 A1 | 8/2013 | Matov et al. | |
| 2015/0002950 A1 | 1/2015 | O'Neill et al. | |
| 2015/0042877 A1 | 2/2015 | O'Neill et al. | |
| 2016/0242870 A1 | 8/2016 | Matov et al. | |
| 2016/0310235 A1 | 10/2016 | Derakhshan et al. | |
| 2017/0273760 A1 | 9/2017 | Morton et al. | |
| 2018/0280118 A1 | 10/2018 | Cramer | |
| 2018/0284580 A1 | 10/2018 | Matthews | |
| 2018/0303579 A1 * | 10/2018 | Salah | A61B 1/0676 |
| 2019/0029784 A1 | 1/2019 | Moalem et al. | |
| 2019/0053876 A1 | 2/2019 | Sterental et al. | |
| 2019/0167115 A1 | 6/2019 | Dorodvand et al. | |
| 2019/0192259 A1 | 6/2019 | Kopelman et al. | |
| 2019/0299055 A1 * | 10/2019 | Poulsen | A63B 23/18 |
| 2019/0328488 A1 | 10/2019 | Levin et al. | |
| 2019/0343601 A1 | 11/2019 | Roschin et al. | |
| 2019/0388193 A1 | 12/2019 | Saphier et al. | |
| 2020/0000552 A1 | 1/2020 | Mednikov et al. | |
| 2020/0000554 A1 | 1/2020 | Makarenkova et al. | |
| 2020/0000555 A1 | 1/2020 | Yuryev et al. | |
| 2020/0085546 A1 | 3/2020 | Li et al. | |
| 2020/0107915 A1 | 4/2020 | Roschin et al. | |
| 2020/0155274 A1 | 5/2020 | Pimenov et al. | |
| 2020/0160947 A1 | 5/2020 | Rasovsky et al. | |
| 2020/0214800 A1 | 7/2020 | Matov et al. | |
| 2020/0281702 A1 | 9/2020 | Kopelman et al. | |
| 2020/0297458 A1 | 9/2020 | Roschin et al. | |
| 2020/0306011 A1 | 10/2020 | Chekhonin et al. | |
| 2020/0306012 A1 | 10/2020 | Roschin et al. | |
| 2020/0315434 A1 | 10/2020 | Kopelman et al. | |
| 2020/0315744 A1 | 10/2020 | Cramer | |
| 2020/0349705 A1 | 11/2020 | Minchenkov et al. | |
| 2020/0360109 A1 | 11/2020 | Gao et al. | |
| 2020/0404243 A1 | 12/2020 | Saphier et al. | |
| 2021/0030503 A1 | 2/2021 | Shalev et al. | |
| 2021/0059796 A1 | 3/2021 | Weiss et al. | |
| 2021/0068773 A1 | 3/2021 | Moshe et al. | |
| 2021/0073998 A1 | 3/2021 | Brown et al. | |
| 2021/0121049 A1 | 4/2021 | Rudnitsky et al. | |
| 2021/0128281 A1 | 5/2021 | Peleg | |
| 2021/0134436 A1 | 5/2021 | Meyer et al. | |
| 2021/0137653 A1 | 5/2021 | Saphier et al. | |
| 2021/0174477 A1 | 6/2021 | Shi et al. | |
| 2021/0196152 A1 | 7/2021 | Saphier et al. | |
| 2021/0282634 A1 * | 9/2021 | Oren-Artzi | A61B 1/042 |
| 2022/0338727 A1 * | 10/2022 | Chambers | A61B 1/0014 |
| 2023/0149129 A1 * | 5/2023 | Oren-Artzi | A61C 7/002 |
| 2023/0293001 A1 | 9/2023 | Zhao et al. | |
| 2024/0122689 A1 * | 4/2024 | Pellissard | H04B 1/3877 |
| 2024/0126153 A1 * | 4/2024 | Pellissard | G03B 17/565 |
| 2024/0164629 A1 * | 5/2024 | Pellissard | A61B 1/0014 |
| 2024/0164631 A1 * | 5/2024 | Eilat-Bloch | A61B 1/0014 |

FOREIGN PATENT DOCUMENTS

| | | | |
|---|---|---|---|
| KR | 101583547 B1 | 1/2016 | |
| KR | 101584737 B1 | 1/2016 | |

OTHER PUBLICATIONS

Designboom; Dental Monitoring Scanbox; 10 pages; Mar. 28, 2020; retireved from the internet (https://www.designboom.com/technology/scanbox-dental-monitoring-teeth-scanner-03-28-2020/) on Jul. 29, 2025.

Glidewell; The Profitability Potential of Glidewell Clear Aligners: Powered by ProMonitoring; 8 pages; May 6, 2025; retrieved from the internet (https://glidewelldental.com/company/blog/the-profitability-potential-of-glidewell-clear-aligners-powered-by-promonitoring) on Jul. 29, 2025.

IDental Shop; Dental Photography Kits; Dental Mentor; 15 pages; Aug. 31, 2020; retreived from the internet (https://identalshop.com/products/dental-photography-kit) on Jul. 29, 2025.

* cited by examiner

100

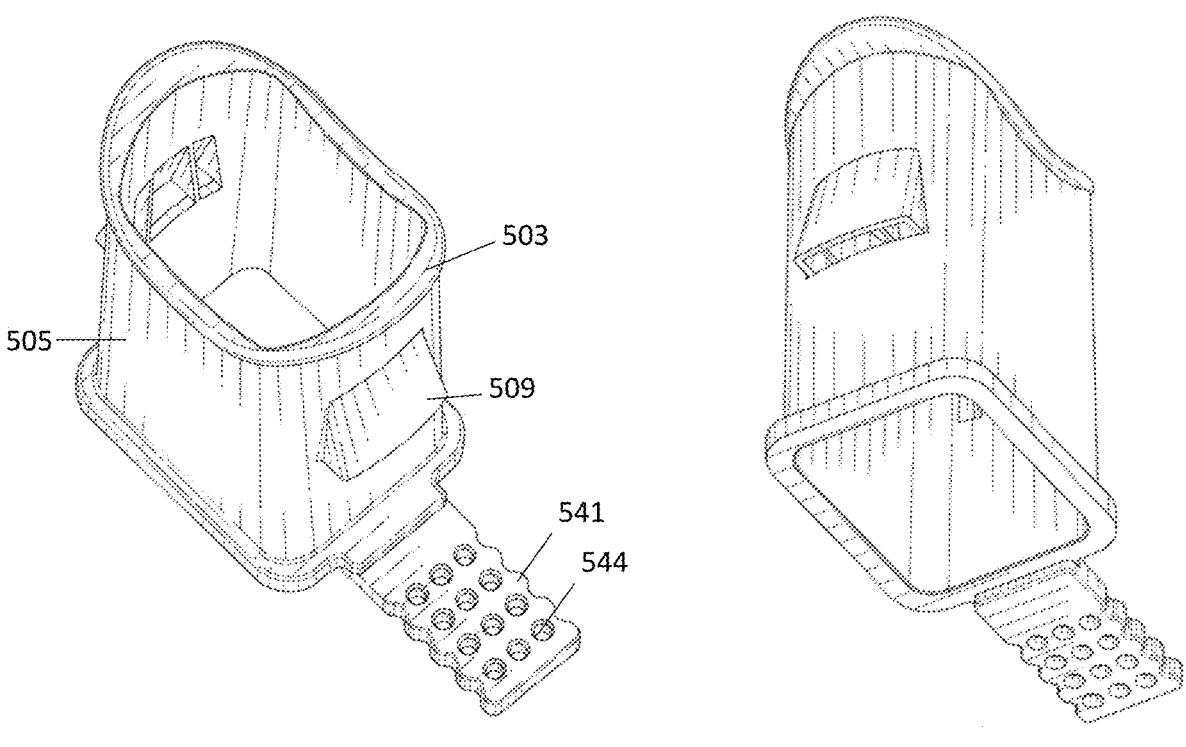
FIG. 5A
FIG. 5B
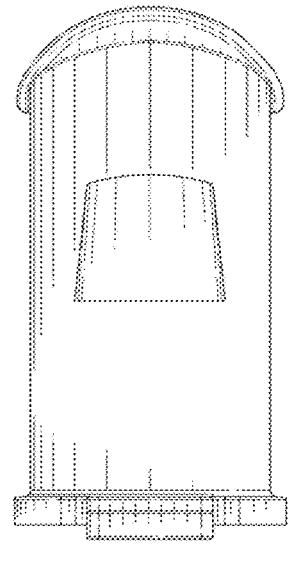
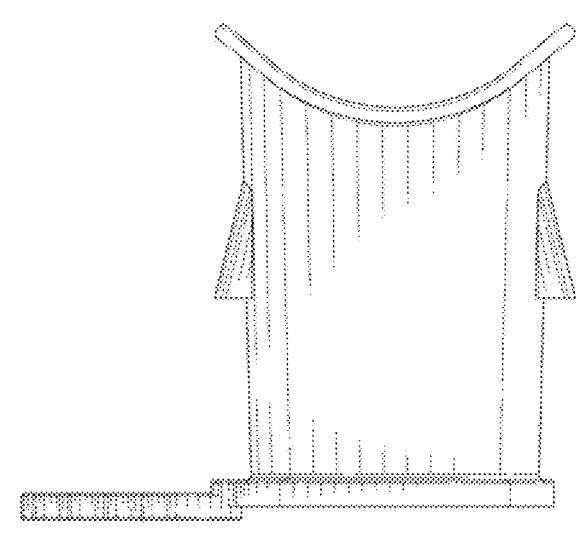
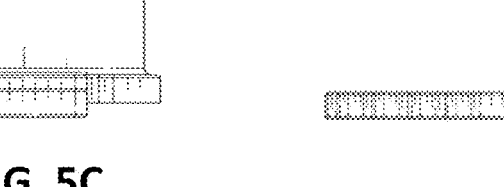
FIG. 5C
FIG. 5D

800

800

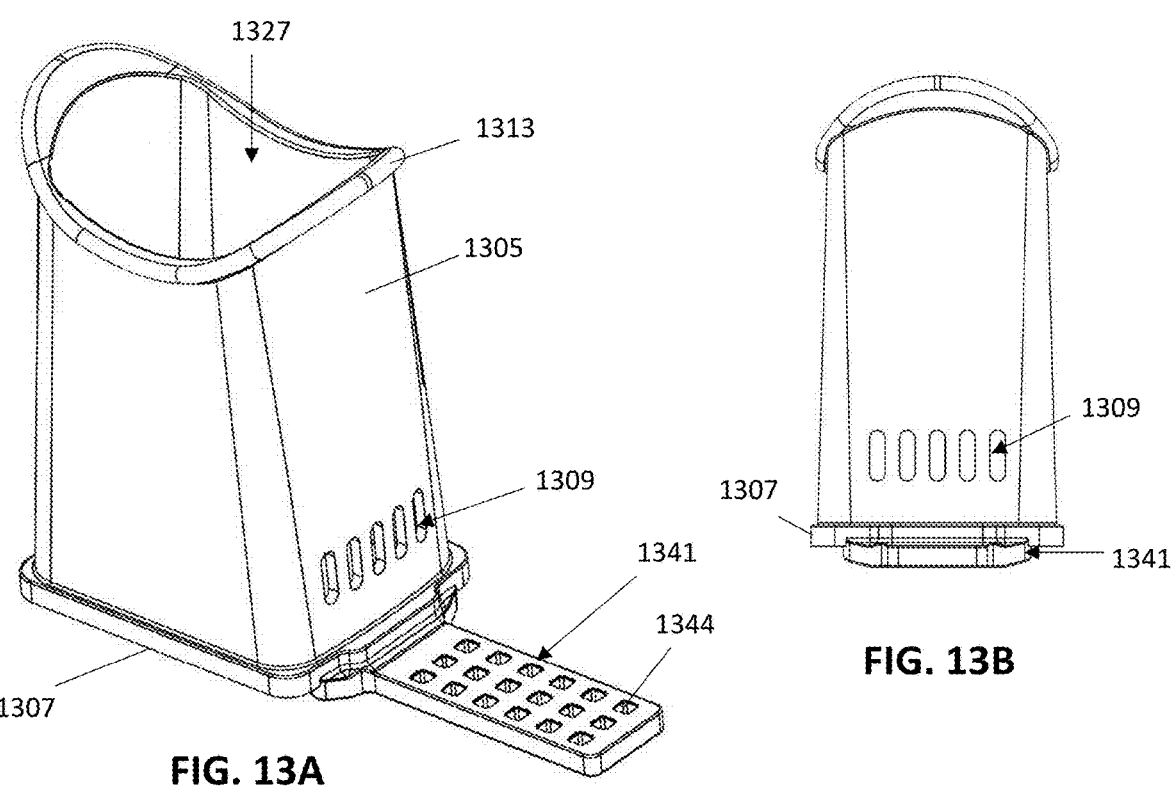
FIG. 13A
FIG. 13B
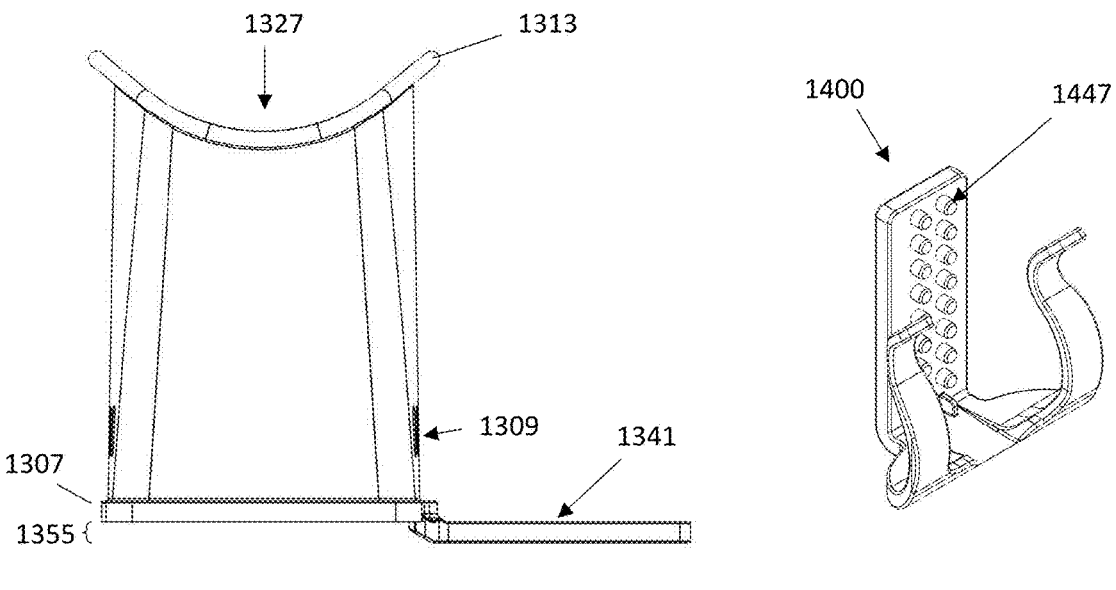
FIG. 13C
FIG. 14

2401

2447

2369

2401

2369          2447

SMARTPHONE DENTAL IMAGING ATTACHMENT APPARATUS

CLAIM OF PRIORITY

This patent application claims priority to U.S. Provisional Patent Application No. 63/180,008, titled "SMARTPHONE DENTAL IMAGING ATTACHMENT APPARATUS," filed on Apr. 26, 2021 and U.S. Provisional Patent Application No. 63/212,583, titled "SMARTPHONE DENTAL IMAGING ATTACHMENT APPARATUS," filed Jun. 18, 2021. This patent application also claims priority as a continuation-in-part to U.S. Design patent APPLICATION No. 29/780,745, titled "DENTAL IMAGING ATTACHMENT FOR A SMARTPHONE," filed Apr. 26, 2021, and U.S. Design patent application No. 29/827,196, titled "DENTAL IMAGING ATTACHMENT FOR A SMARTPHONE," filed Feb. 17, 2022, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

It is often important to image a patient's teeth before and during an orthodontic treatment. Orthodontic procedures typically involve repositioning an individual's teeth to a desired arrangement in order to correct malocclusions and/or improve aesthetics. Treatment planning may include uses a 3D dental model created from a scan or dental mold of an individual's teeth. The 3D dental model can comprise, for example, raw tooth point clouds, tooth meshes, or reduced parameter representations of 3D teeth.

At the start and/or during the course of a treatment plan implementation, it may be beneficial for the patient (or a caregiver such as a parent) to take one or more images of a patient's teeth that may be used to help in treatment planning or in monitoring treatment planning. It would be particularly helpful to provide one or more means for a patient or caregiver to take images using a readily available smartphone, rather than requiring the use of a professional dental camera or imaging system.

SUMMARY OF THE DISCLOSURE

Described herein are methods and apparatuses that may provide low-cost and simplified ways to take images of a patient's teeth using a patient's own smartphone. These images may be taken at a precise position, automatically retracting the patient's lips, and providing imaging enhancements as part of a robust, hand-held system. In particular, described herein are smartphone dental imaging apparatuses (e.g., systems, devices, etc.).

These smartphone dental imaging apparatuses may be configured as smartphone attachments for taking high quality intraoral images of patient dentition at home or clinic. The attachment-patient interface may be configured to avoid excessive strain on the patient's intraoral cavity. These apparatuses provide a convenient patient interface, allow smartphone clip-on, and avoid fogging or fouling of the lens of the smartphone camera. These apparatuses may include or may be used with one or more processing algorithms that may improve the image quality. These apparatuses provide high-quality blur-free occlusal imaging. These apparatuses may also provide shade-free illumination using built-in smartphone light.

These methods and apparatuses may provide techniques (e.g., methods) and apparatuses for the patient or caregiver to assist in tracking or monitoring of a treatment plan without requiring the use of expensive or complex devices. For example, described herein are methods and apparatuses that may be used with a patient or caregiver's personal phone. In some examples, an attachment or other device may be coupled to the patient or caregiver phone; these accessory devices may be adapted for use with software, hardware or firmware for assisting in taking images (or guiding a user subject to take images) of sufficiently high quality so that the images may accurately track the patient's teeth in a treatment plan.

Of particular interest herein are methods and apparatuses for assisting a subject, e.g., a patient or caregiver (e.g., parent, guardian, etc.), collectively referred to herein as a "user subject", in collecting one or more images of sufficient size and with sufficient information about distance from the teeth, etc., so as to capture enough of the dentition so that it may be readily analyzed by one or more automated agents (including machine learning agents, other software, etc.) and/or manual agents (e.g., technician, dental professional, etc.). Although in the user subject may be distinct from the user professional, the user subject may be a professional user. For example, a professional user may use the methods and/or apparatuses described herein on a patient, and therefore act as both the user subject and the professional user.

In some examples, the user subject may be directed to take multiple images of the patient's teeth and/or oral cavity using a phone camera to which the apparatus is coupled. The Apparatus may automatically adapt to a variety of different user phone configurations and may be robust and simple to use.

In general, the apparatuses described herein are imaging apparatus that are adapted to couple to virtually any smartphone and that have a body including a tubular channel and a mouth insert that is configured to be secured in the patient's mouth to hold the device is a predefined position, with the lips retracted, so that the teeth may be consistently and reliably imaged. These apparatuses may be particularly configured so that the light quality is maintained and so that the device does not fog or occlude the camera on the phone. In addition, these apparatuses may be configured to releasably engage with a variety of phone types, regardless of the dimensions of the phone or the position of the camera.

In general, there are a variety of phones in use by patients that may position one or more cameras on different locations on the phone, including but not limited to the corner of the phone. The apparatuses described herein may provide a "universal" adapter configuration that may allow the apparatus to be used with a variety of different phone types, including but not limited to those with phones on the corner and/or near a center of the phone. The apparatuses described herein may therefore be referred to as "universal".

In general, the apparatuses described herein may include a patient interface (e.g., lip retractor portion) that is also configured with a shape that allows it to be used by a large number of patients without interfering with the imaging quality when imaging the teeth. The patient interface region is also configured so as to be used with a large number of patients of different sizes and ages. These apparatuses may also include an elongate cylindrical (tube) body region; the tube region separates the patient interface (and therefore the teeth of the patient) from the camera by a predetermined distance that is configured to allow clear imaging while separating the lens(es) of the apparatus from the mouthpiece to prevent fogging. In addition, the cylindrical body may include one or more vents. The cylindrical body may be tapered. In some examples, the cylindrical body tapers from a narrower base at the smartphone interface region and widening gradually towards the patient interface region. In some examples the cylindrical body tapers from a broader base at the smartphone interface and narrowing gradually towards the patient interface region. The taper may be between 5 degrees and 30 degrees (e.g., between 5 degrees and 20 degrees, etc.).

The base may generally be configured as a smartphone interface region and may be couple to (or to be integral with) a clamp, clip or other releasable attachment mechanism, including a universal attachment, for coupling to a smartphone.

Any of these apparatuses may also be configured to operate with software, including in particular, with a smartphone application software, that may coordinate operating the apparatus to take one or more images of the patient's oral cavity (e.g., teeth, gums, gingiva, arch, etc.).

Thus, these apparatuses may therefore combine a cheek/lip retractor (generically referred to herein as a cheek retractor) and a phone/camera holder. In some cases, these apparatuses may include two (or more) pieces, such as a releasable phone attachment portion and a mouthpiece/spacer portion, including the cheek retractor and tubular body. The applicator software (e.g., app) may also be part of this system.

In any of these apparatuses the universal adapter (also referred to herein as a phone attachment) may be a clamp as described above, and may be integrated together with, or may be separate and connectable to, the patient interface and tubular body.

In general, the universal adapter for releasably coupling to the phone may be configured as a clip or clamp that is configured to grip and secure to the back and sides of the phone without blocking or contacting the front (e.g., screen) of the phone. In some examples the adapter may have three (or more) operating positions, including a first position in which the adapter is loosely held on the phone, but can be moved around the edge(s) and/or back of the phone to position the tubular body over the one or more cameras, and a second, locked position, in which the tubular body is locked in position until it is intentionally released. A third, unlocked/unattached position allows the adapter and apparatus to be removed from the phone.

For example, the phone attachment may be a clip-on clamp that couples to the sides and/or back of the user's phone. The phone attachment may grasp and secure to the phone from a side (or sides) of and back of the phone. In general, the phone attachment, and therefore the apparatus, does not cover up the front, and in particular the screen, of the phone. The phone attachment may include three states. In the first state the phone attachment may be coupled to the body of the phone so that the position of the phone relative to the patient interface and tubular body may be adjusted. The phone attachment may be loosely coupled to the body of the phone. Alternatively or additionally, the phone attachment may be coupled to the body of the phone but the connection to the patient interface and tubular body portions may be adjusted. This may allow the apparatus to be finely positioned relative to the phone body and in particular, relative to the camera(s) of the phone. The apparatus may then be transitioned to a secured configuration in which the patient interface and tubular body is rigidly coupled to the phone body through the phone attachment. Finally, the apparatus may be disengaged from the phone body by fully disengaging the phone attachment from the phone body.

The opening at the patient interface may be configured to comfortably fit within a variety of patient mouth sizes comfortably, while still maximizing the field of view as much as possible. For example, the patient interface may have a maximum outer diameter in the length dimension that is between 75 and 60 mm (e.g., between about 70-60 mm) and in the width dimension by about 45-30 mm (e.g., between about 40-35 mm). The patient interface may generally be saddle-shaped.

The length of the tubular body may also be configured to optimize the focus and field of view. For example, the length of the tubular body from the base where it interfaces with the phone to the patient interface may be between about 70-95 mm (e.g., between about 75 and about 90 mm). Shorter body lengths generally lead to larger field of view, but may be more difficult to focus, while longer body lengths may have narrower fields of view.

The apparatuses described herein may also generally be configured and adapted to avoid or reduce fogging or fouling of the camera from the patient's breath. Any of these apparatuses may include one or more passive venting chambers, e.g., positioned on the tubular body. In some examples the tubular body may be more open, e.g., may include one or more windows or openings through the body. However, it may be beneficial to enclose the tubular body to control lighting, prevent shadows, etc. In some examples the wall(s) of the tubular body may be adapted and configured to reflect light and/or help uniformly illuminate the oral cavity for taking images. For example, the tubular body may include a soft lighting, reflective body (e.g., formed of a light-diffusing material, such as an opaque polymeric material), and/or a material having a light-diffusing texture or coating. In some examples a portion of the elongate body may be formed of a reflective material. In some examples the elongate body may include one or more light pipes to help diffuse light within the elongate body to illuminate the oral cavity (e.g., teeth, gingiva, etc.) more uniformly.

In some examples the patient interface (e.g., mouthpiece) and/or the elongate tubular body may be pivotally connected, so that different angles of images may be taken relative to the patient's oral cavity. Alternatively, in some examples the patient interface, elongate tubular body and phone attachment may be coupled rigidly together to prevent movement relative to each other.

The patient interface may include a saddle-shaped rim extending proud of the tubular body, that may be configured for placing behind the user's lips, to retract and hold the lips apart from the rest of the oral cavity while taking the image. The saddle-shaped patient interface may include a lip or rim region extend between 3-8 mm from the elongate body. The rim may be rounded to prevent pinching or harming the gums and lips. The rim may have a generally oval outer shape, and may be curved away from the tubular body, so as to confirm to the teeth. The curvature (arc) of the patient-facing side of the patient interface may approximately mimic the curvature of patient's dentition (e.g., gums). The patient interface is generally configured to be easily inserted and removed from the patient's mouth.

In some examples, as mentioned above, the patient interface and elongate body may form one portion of the apparatus and may be removably coupled to the phone attachment portion. This may allow the patient interface to be separately cleaned, including within a dishwasher or other device.

Although many of the examples described herein may be used without additional lenses or other optical components (other than the elongate tube body), in some examples the apparatus may include additional lenses, light sources, etc. For example, focusing optics may be included. Ins some example, one or more illumination sources (e.g., LEDs) may be included. Also described herein are methods and systems for monitoring a dental subject's progress during a course of treatment. At any particular point in time during the course of treatment, a model (one or more 2D images, a 3D model, etc.) of the expected positions of the subject's teeth at that point in time can be compared with one or more images of the subject's teeth taken during the course of treatment using any of these apparatuses. During the course of treatment, a camera phone may be used with any of these apparatuses to take a two-dimensional (2D) image of the subject's teeth. The 2D image represents the actual positions of the subject's teeth at that particular point in the orthodontic treatment.

The monitoring system can compare the input 2D image to the rendered 2D image to determine how closely the actual or current position of the subject's teeth tracks with the expected or desired positions according to the orthodontic treatment plan.

The subject may use an application software (e.g., "app") for their hand-held device, such as a smartphone, in conjunction with any of these apparatuses. The application software may guide the subject in taking the image(s), and may process the image(s), e.g., locally using the one or more processors in the hand-held device, or remotely by passing the image onto a remote server.

Other examples of techniques and systems that may benefit from the methods and apparatuses described herein may be found, for example, in U.S. patent application Ser. No. 16/370,788, filed on Mar. 29, 2019 (titled "PHOTOGRAPH-BASED ASSESSMENT OF DENTAL TREATMENTS AND PROCEDURES"), which is a continuation of U.S. patent application Ser. No. 14/831,548, filed on Aug. 20, 2015 (titled "PHOTOGRAPH-BASED ASSESSMENT OF DENTAL TREATMENTS AND PROCEDURES"), which issued on Apr. 2, 2019 as U.S. Pat. No. 10,248,883. Each of these applications is herein incorporated by reference in its entirety.

In general, the methods and apparatuses described herein may be performed at very low cost and complexity for subject at-home monitoring, without requiring a dental practitioner or expensive scanning equipment.

For example, described herein are systems (e.g., smartphone dental imaging apparatuses, the system comprising: a tubular body having a central lumen extending therethrough, from a first end to a second end; a patient interface on the first end of the tubular body, wherein the patient interface comprises a saddle-shaped mouth region having a rim extending at least partially around the circumference of the first end of the tubular body and configured to fit between a patient's lips and gums; and a smartphone interface at the second end of the tubular body, wherein the smartphone interface comprises: a camera opening configured to fit over a camera of a smartphone; a base projection extending perpendicularly from the tubular body at the second end; and a clip or clamp configured to clamp or clip to one or more sides of a smartphone, the clip or clamp further comprising a plate including an array of projecting members extending from the plate and configured to engage the base projection against the patient's smartphone.

For example, a system (e.g., a smartphone dental imaging apparatus) may include: a tubular body having a central lumen extending therethrough, from a first end to a second end; a patient interface on the first end of the tubular body, wherein the patient interface comprises a saddle-shaped mouth region having a rounded rim extending between 3 mm and 10 mm around the circumference of the first end of the tubular body and configured to fit between a patient's lips and gums; and a smartphone interface at the second end of the tubular body, wherein the smartphone interface comprises: a camera opening into the lumen and configured to fit over a camera of a smartphone; a base projection extending perpendicularly from the tubular body at the second end, the base projection comprising a plurality of engagement openings; and a clip or clamp configured to clamp or clip to one or more sides of a smartphone, the clip or clamp further comprising a plate including an array of projecting members extending from the plate and configured to engage the engagement openings of the base projection.

The tubular body may comprise a diffusive material configured to diffuse light within the lumen, as mentioned above. The diffusive material may be a coating, or, in some examples, the tubular body may be formed of a light-diffusing material (such as an opaque and/or translucent material).

In any of the apparatuses (e.g., systems) described herein the rim may extend as a flanged edge on either end of the first side of the tubular body. For example, the rim may include a pair of sections (flange sections) on opposite sides of the first end that flair outwards to form the saddle shape. In some examples a region of the first end of the tubular body between the pair of sections does not include a flange. The region between the flanges that may fit into the mouth (e.g., between the cheeks and the teeth) may be a cut-down region that extends distally away from the first end.

In any of the apparatuses (e.g., systems) described herein, apparatus may include a frame portion that couples to the second end (e.g., second end region) of the tubular body. The base projection portion of the apparatus may be a part of the frame, e.g., it may be integral to the frame, or it may be coupled to the frame. The frame may be part of the smartphone interface. The frame may be configured to attach to the tubular body at multiple configurations, so that attaching at a first region near an upper end of the frame (opposite from the base projection) may result in the apparatus having a longer length from the first end to the camera opening, while attaching at a second region at or near the lower end of the frame (e.g., closer or adjacent to the base projection) may result in the apparatus having a shorter length from the first end to the camera opening. For example, the smartphone interface may include a frame configured to couple to the second end of the tubular body to form the camera opening, wherein the base projection is integral with or coupled to the frame.

The tubular body may be straight or tapered, e.g., tapered from the first end to the second end. The tubular body may optionally comprise one or more air vents configured to permit the passage of air but limiting the passage of light into the lumen from outside.

In some examples the tubular body extends between 70 mm and 95 mm in length (e.g., between 75 and 90 mm, etc.). This length may allow ease of use and focusing of the phone camera onto the dentition (e.g., teeth, gingiva, etc.).

The rim of the patient interface may extend proud of the tubular body. The patient interface may form an opening into the lumen that is, e.g., between 50 mm and 70 mm long (e.g., between 35 mm and 50 mm wide).

The smartphone interface may include a gasket, e.g., around the second end, to prevent light from entering the lumen between the smartphone and the second end. The gasket may be a compressible material (e.g., silicone, foam, etc.).

The base projection may comprise a plurality of openings configured to engage with the array of projecting members. The projecting members may be pegs or may include an interlocking portion that may engage securely within the openings. The projecting members may equivalently be on the base projection and the openings may equivalently be on the plate.

In some examples the clip or claim may be a clamp formed by two or more pieces configured to be secured together to apply compression to the subject's phone.

As mentioned, described herein are apparatuses (including systems) for taking one or more adapting a smartphone to take images of a patient's dentition (e.g., teeth, gums, etc.). For example, a system as described herein may include: a tubular body having a central lumen extending therethrough, from a first end to a second end; a patient interface on the first end of the tubular body, having a rim configured to fit between a patient's lips and gums; and a smartphone interface at the second end of the tubular body, wherein the smartphone interface comprises: an annular base region forming an opening into the central lumen that is configured to fit over one or more camera of a smartphone; and a base projection extending parallel to the annular base region and laterally offset from the annular base region; and a securement configured to clamp or clip to one or more sides of a smartphone to hold the base projection against a back of the smartphone, wherein the securement comprises a plate including an array of attachments configured to engage complementary attachments on the base projection, wherein the annular base region is configured to cantilever over the back of the smartphone when the base projection is held against the back of the smartphone by the securement. The annular base region may cantilever between 2 mm-15 mm over the back of the smartphone when the base projection is held against the back of the smartphone by the securement.

In any of these examples, the securement is hinged to the annular base region and/or the tubular body. The securement may comprise a clamp formed by two or more pieces configured to be secured together to apply compression to the subject's phone. In some examples the securement comprises a clip.

For example, a system may include: a tubular body having a central lumen extending therethrough, from a first end to a second end; a patient interface on the first end of the tubular body, having a rim configured to fit between a patient's lips and gums; and a smartphone interface at the second end of the tubular body, wherein the smartphone interface comprises: an annular base region forming an opening into the central lumen that is configured to fit over one or more camera of a smartphone; and a base projection hinged to the annular base region, the base projection having a folded configuration in which the base projection is parallel to the central lumen of the tubular body and a deployed configuration in which the base projection extends parallel to the annular base region and is laterally offset from the annular base region; and a securement configured to clamp or clip to one or more sides of a smartphone to hold the base projection in the deployed configuration against a back of the smartphone, wherein the securement comprises a plate including an array of attachments configured to engage complementary attachments on the base projection, wherein the annular base region is configured to cantilever over the back of the smartphone when the base projection is held against the back of the smartphone by the securement.

Also described herein are methods of capturing one or more images of a patient's teeth using any of these apparatuses. For example, a method may include: attaching a base projection of a smartphone imaging adapter against the back of a smartphone so that an annular base region forming an opening into a central lumen of a tubular body is positioned over one or more cameras of the smartphone; securing the base projection region to the back of the smartphone by attaching a securement to the base projection region, so that the annular base region is held cantilevered over the back of the smartphone with a gap of between 2-15 mm between a bottom of the annular base region and the back of the smartphone; and taking one or more image of the patient's teeth through the central lumen of the tubular body.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 5A-5D show top perspective, bottom perspective, side and front view, respectively, of one example of a smartphone imaging apparatus as described herein.

FIG. 8A shows a front perspective view, while FIG. 8B shows a back side view.

FIGS. 13A-13C illustrate another example of a portion of an imaging apparatus as described herein. FIG. 13A shows a front perspective view. FIG. 13B shows a side view. FIG. 13C shows a front view.

FIG. 14 illustrates another example of a securement similar to that shown in FIG. 6, having cylindrical attachment engaging members. The securement may be part of a system, including a system for dental imaging using a smartphone.

FIGS. 22A-22C show perspective views of the smartphone imaging apparatus; FIGS. 22D and 22E show exploded views of the smartphone imaging apparatus.

FIG. 23A shows a top perspective view and FIG. 23B shows a bottom perspective view.

FIG. 24A shows a top left perspective view and FIG. 24B shows a top right perspective view.

DETAILED DESCRIPTION

Described herein are apparatuses (e.g., systems, computing device readable media, devices, etc.) and methods for monitoring, analyzing, correcting and/or tracking the progress of a subject's orthodontic treatment. In the particular, described herein are apparatuses for capturing and recording images of the subject's teeth (input 2D image) with a smartphone that are smartphone add-on devices that are capable of adapted to a variety of different smartphones and taking high-quality color dentition images using the smartphone rear camera(s) and flash. The add-on includes all features required for imaging buccal, lingual and occlusal images without requiring an additional (separate) cheek retractor.

In general, these apparatuses may include a patient interface region configured to be held in the subject's mouth and retract the lips/cheeks and a tubular body region, and a smartphone interface region. The smartphone interface region may be configured as a universal adapter for coupling to a variety of different smartphone shapes and types without obscuring the screen of the smartphone or interfering with controls on the smartphone, including on the sides of the smartphone.

The apparatuses described herein, which may be referred to as a smartphone add-on, may include a plastic tubular body ("tube") having an approximately oval cross section. One end of the apparatus is configured as a patient interface and is configured to fit into the patient's mouth to hold it open relative to the inside of the tube enough to enable imaging of buccal, lingual and/or occlusal imaging of the patient's teeth and/or gingiva. The second end of the apparatus may be either adapted to attach to a smartphone rear camera or to couple to as separate smartphone interface for coupling the tubular body to the camera.

Figure 1A:
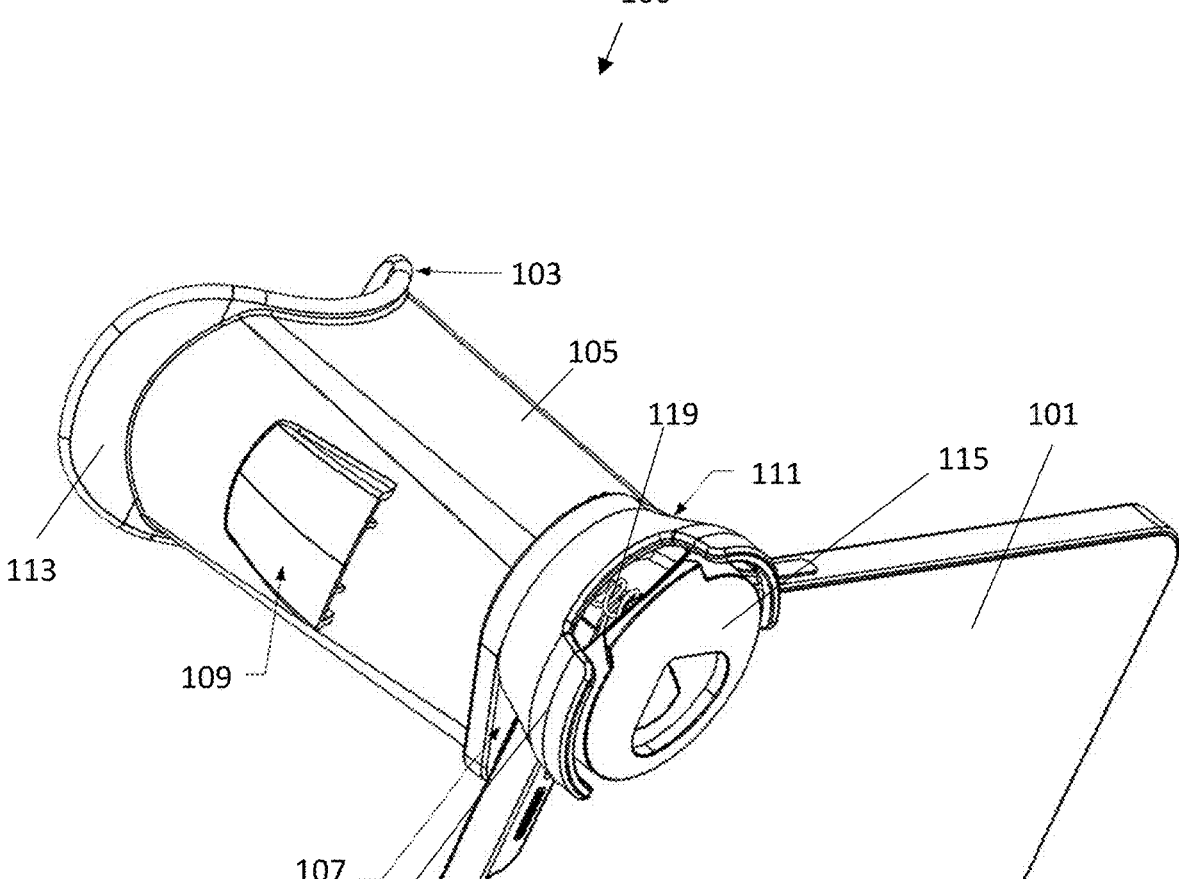
FIG. 1A shows one example of an imaging apparatus, e.g., a smartphone imaging apparatus, coupled to a smartphone as described herein.
Figure 1B:
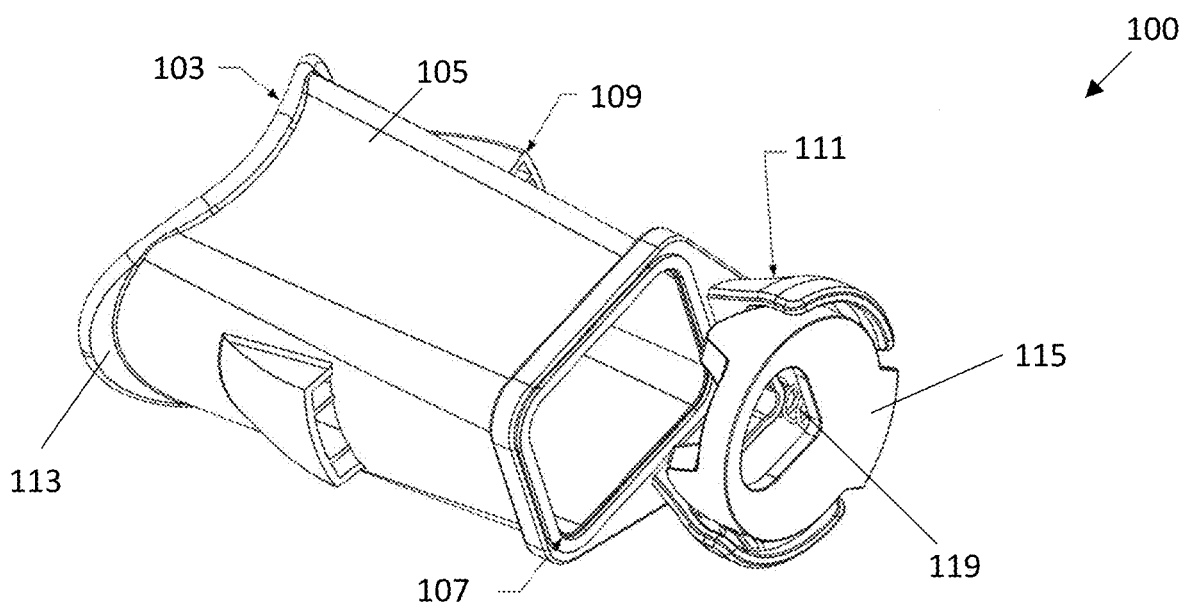
FIGS. 1B and 1C show alternative views of the apparatus of FIG. 1A.
Figure 1C:
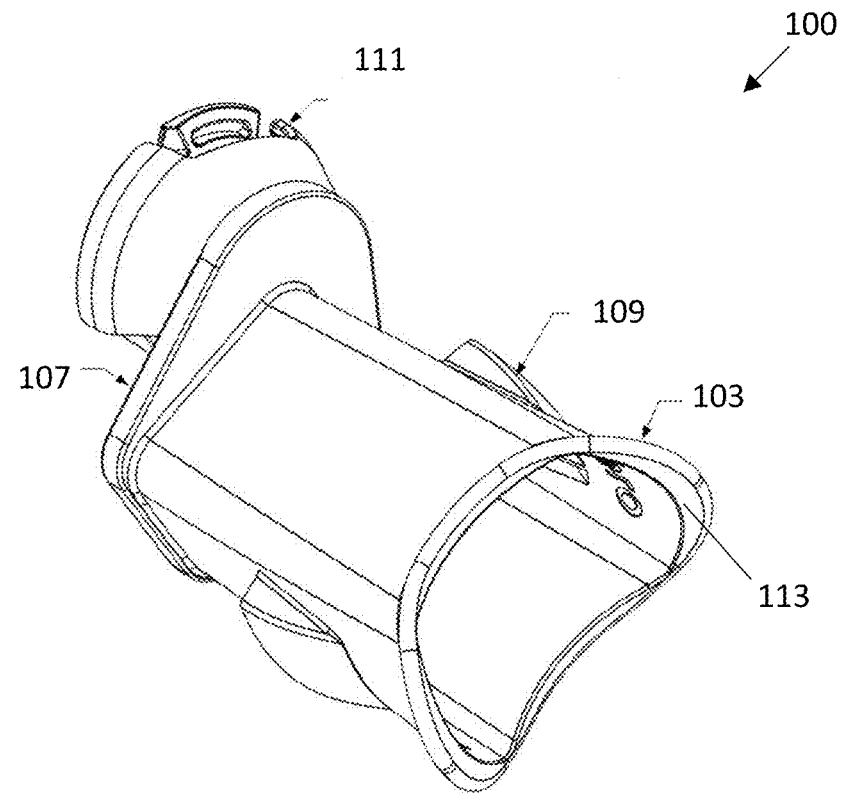

For example, FIGS. 1A-1C illustrates one example of a smartphone dental imaging apparatus as described herein. In FIG. 1A, the apparatus 100 includes an elongate tubular body 105. In this example, the tubular body tapers slightly from the first end, forming the patient interface 103 to a second end, forming (or attached to) the smartphone interface 107. In this example, a pair of vents 109 are formed about a third of the way along the tubular body (on the half of the tubular body closer to the patient interface). The vents are formed so that they allow airflow into/out of the tubular body, to reduce moisture, but to prevent light entering or escaping the tubular body, which may generate shadows.

In FIG. 1A, the apparatus 100 forms the patient interface 103 at the first end. The patient interface has a curved, shape and includes a rim 113 that is rounded and atraumatic to fit between the patient's lips and their gums with the mouth either opened (with space between the teeth) or closed (to allow intercuspation of the upper and lower teeth). In FIG. 1A the apparatus also includes a smartphone interface 107 that is formed at the second end which engages a clip-on portion 111.

In this example, the clip-on portion captures the user's smartphone 101 between a first clamping portion 115 and a second clamping portion 117 of the clip-on region to secure the corner of the smartphone between these portions. The smartphone interface also includes a bias 119 (shown as a spring) that can apply a biasing force to compress the smartphone between the first and second clamping portions. In this example, the clip-on portion is configured having the first portion hinged to the second portion, and the bias on one side of the spring, driving the clamp closed. The clip-on region also includes a thumb region that is configured to be pushed to open the clamp of the smartphone interface to allow it to be adjusted or removed.

In FIGS. 1A-1C the clamp may be formed as part of the end of the tubular body 105 (e.g., integrated with). In some examples, the smartphone interface may be removably or releasably coupled to the clip-on (or other attachment region).

The tubular body of the apparatus may be passive, with no auxiliary optics or electronics. Thus, the apparatus may instead utilize the smartphone's camera(s) and flash LED to acquire video and still images of the patient dentition. These apparatuses may be configured for use with virtually any smartphone model by providing adjustability/adaptability to fit the rear camera cluster of the smartphone. The same tube may be used with either different smartphone interfaces (modules) or the different smartphone interfaces. In some cases, the smartphone interface may be a universal adapter that may engage with a variety of smartphone configurations. In general, these apparatuses do not require removal of a phone protective case (e.g., for cases having with up to 1.5 mm wall thickness).

In use, the apparatus may be attached to and detach from a user's smartphone by the user. The user may insert her or his mouth over the patient interface portion and may take an image, requiring no special user/patient skills. The apparatus may be operated with a single hand. As mentioned above, during use the apparatus may only minimally block (or not block) the smartphone display screen. Further, the apparatus may avoid obstructing the smartphone buttons; in particular the smartphone interface (e.g., clamp, clip-on, etc.) may avoid blocking or interfering with the smartphone buttons.

Figure 2:
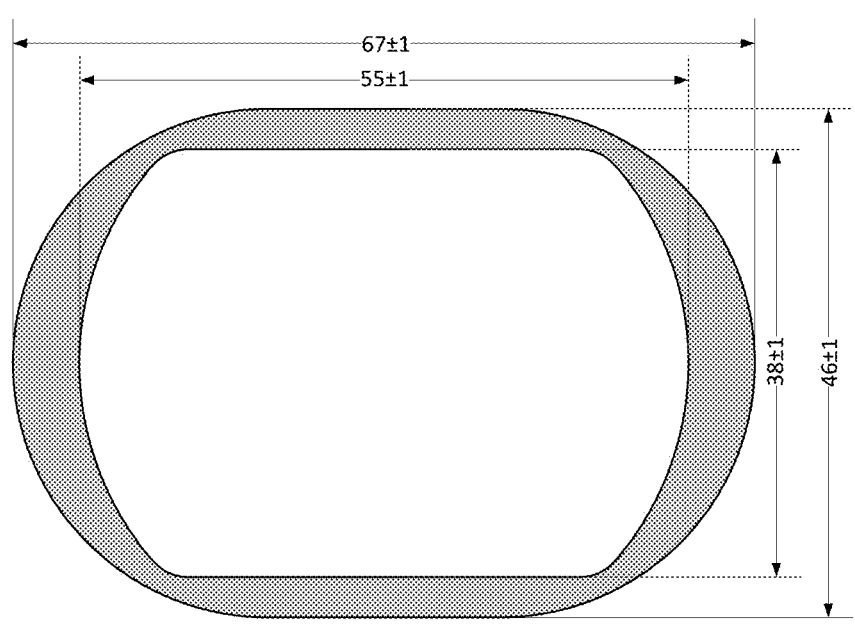
FIG. 2 illustrates one example of the field of view of one example of a smartphone imaging apparatus as described herein.

The patient interface may be configured to provide minimal discomfort for the patient when inserting, removing and taking images using the apparatus. For example, FIG. 2 illustrates one example of a mouthpiece portion of an apparatus, showing an end view of the edge or rim (e.g., lip) of the mouthpiece portion, with exemplary dimensions. Other dimensions (e.g., +/−5%, 10%, 15%, 20%, 25%, 30%, etc.) may be used. In this example the mouthpiece region may has a length of between about 50 mm to about 75 mm (e.g., between about 55 mm to about 67 mm in FIG. 2), and a width of between about 35 and about 55 mm (e.g., between about 38 mm and about 46 mm is shown in FIG. 2).

When taking images, the apparatus may take occlusal images by tilting the apparatus (e.g., the tubular body) up and down. The apparatus may allow taking of buccal images by shifting the tubular body left and right about patient's dentition. The adaptability range of the apparatus may enable imaging of all angles specified without clipping dentition image.

The tubular body may be formed as a diffusive white wall for shadow-free imaging. In general, the apparatus may be configured to withstand dropping or impact without damage (e.g., after being dropped on hard floor from 1-meter height). As mentioned, the entire apparatus (or in some examples, the tubular body and patient interface, which may detach from the smartphone interface portion) may be dishwasher safe and compatible with common household detergents to allow cleaning/disinfection.

Figure 3:
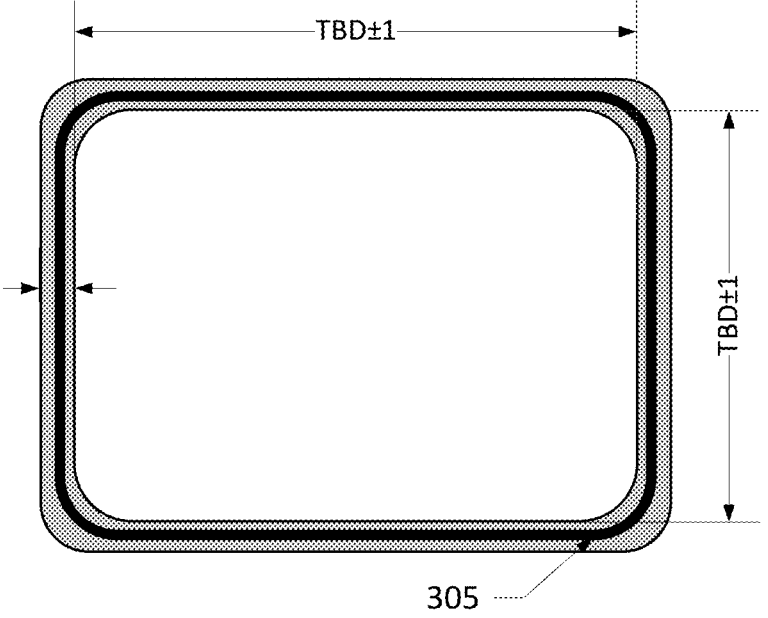
FIG. 3 shows an example of the smartphone adapter end of the imaging apparatus as described herein.

The smartphone interface end region may be configured to have a circumference so as to attach over an entire rear camera/LED cluster for most smartphones, as described in FIG. 3. In this example, the smartphone interface region may be formed at the end of the tubular body; FIG. 3 shows an exemplary wall thickness (e.g., between about 0.3 mm and 2 mm) and may include a gasket 305 around the base of the tubular body wall that may fit against the phone. The gasket may allow the tubular body to conform to the curved or slightly irregularly-shaped body to prevent light from entering the tubular body and interfering with the illumination of the teeth/mouth. The end of the tubular body may also be adapted to engage (e.g., releasably engage) with an adapter, such as a clamp, of the smartphone interface.

Figure 4:
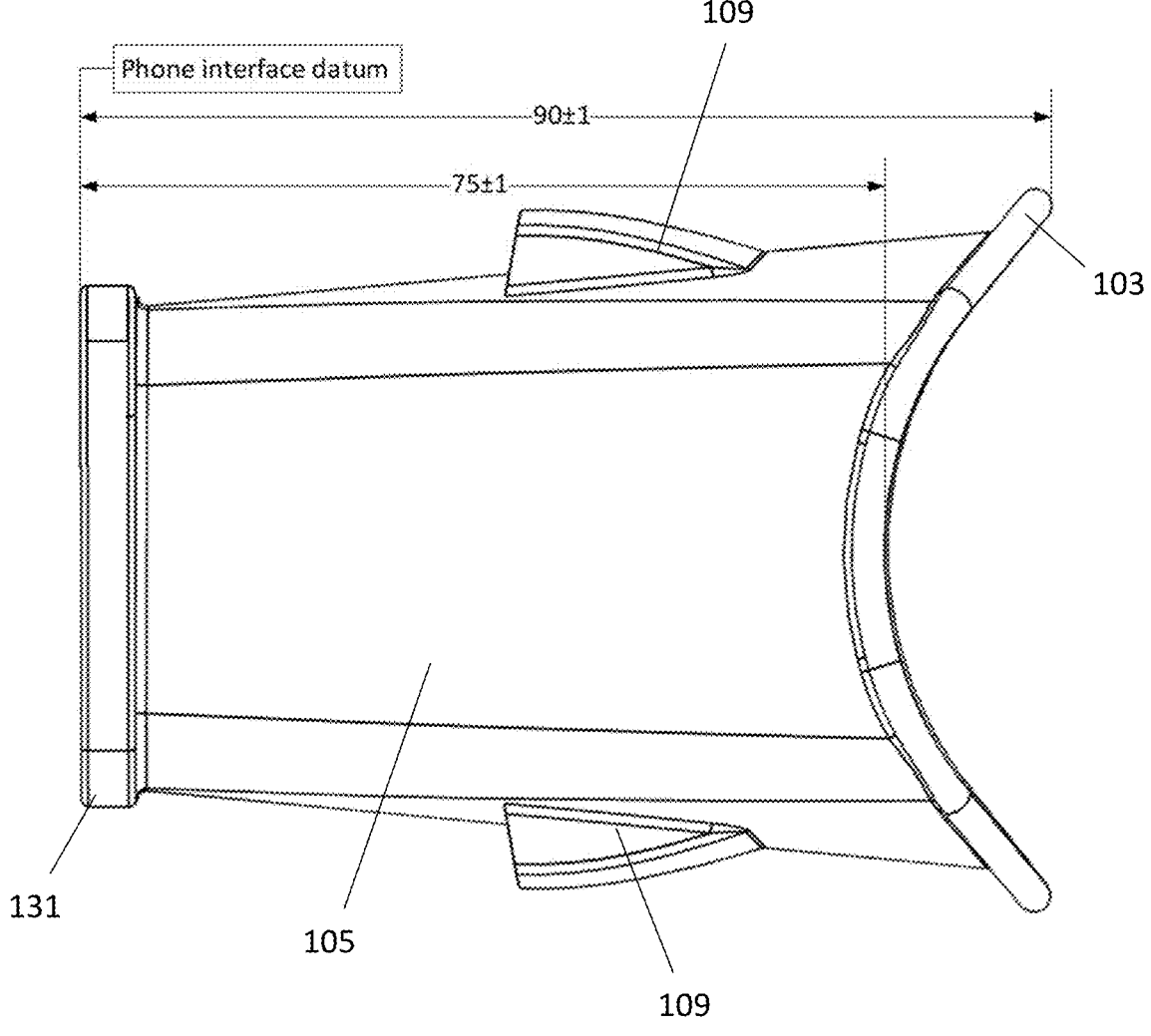
FIG. 4 is a side view of one example of an imaging apparatus as described herein.

FIG. 4 shows an example of a side view of one example of a tubular body 105 (including the patient interface 103 region and a pair of vents 109). FIG. 4 also includes a base portion 131 that may be part of the smartphone interface or may be configured to couple with the smartphone interface. This example also includes exemplary dimensions. For example, the tubular body may have a length of between about 70 mm and about 95 mm. In the non-limiting example shown in FIG. 4, the tubular body has a length of between about 75 mm and about 90 mm. FIG. 4 also shows the saddle-shaped curvature of the patient interface region 103.

FIGS. 5A-5D illustrate another example of an apparatus as described herein. In FIG. 5A, the apparatus includes a tubular body 505 that is not tapered (as in FIGS. 1-4) but includes a pair of vents 509 and also includes a patient interface region 503. The example shown in FIGS. 5A-5D also includes a base projection 541 of the smartphone interface. This base projection 541 extends from one side of the tubular body 505 and may couple with the releasable attachment that couples to the phone (e.g., clamp, clip, etc.).

Figure 6:
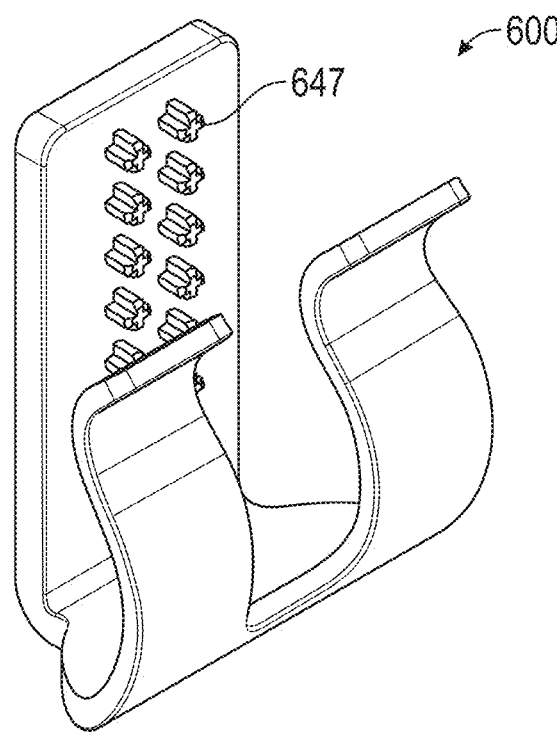
FIG. 6 shows one example of a phone attachment clip for an apparatus as described herein, including a flexural clip-on base for coupling the tube portion of the smartphone apparatus to the phone.

In the example shown in FIGS. 5A-5D the base projection 541 extends perpendicularly from the central axis of the tubular body 505 and includes an array of openings 544 into which the releasable attachment may couple to secure the apparatus to the phone. For example, FIGS. 6-8B illustrate examples of releasable attachments forming adapters for coupling the tubular body to the patient's phone. In FIG. 6 the clip 600 shown includes an array of projecting members 647 (also in FIG. 7, 747) extending from a plate that will engage with the base projection similar to that shown in FIG. 5A-5D and provide a stable engagement with the tubular body and the rest of the apparatus.

Figure 7:
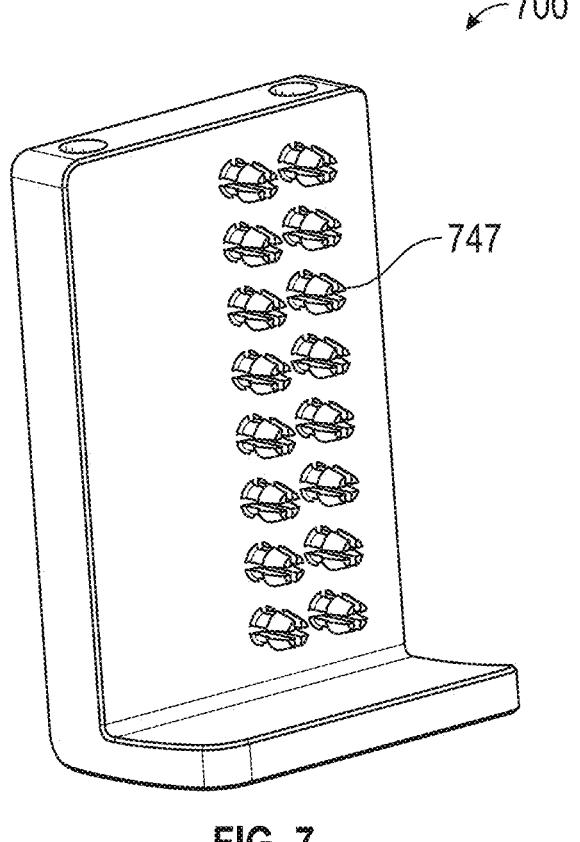
FIG. 7 shows one example of a phone attachment base for an apparatus as described herein, forming a bracket with tube attach pins, that may clamp to a phone on its sides.
Figure 8A:
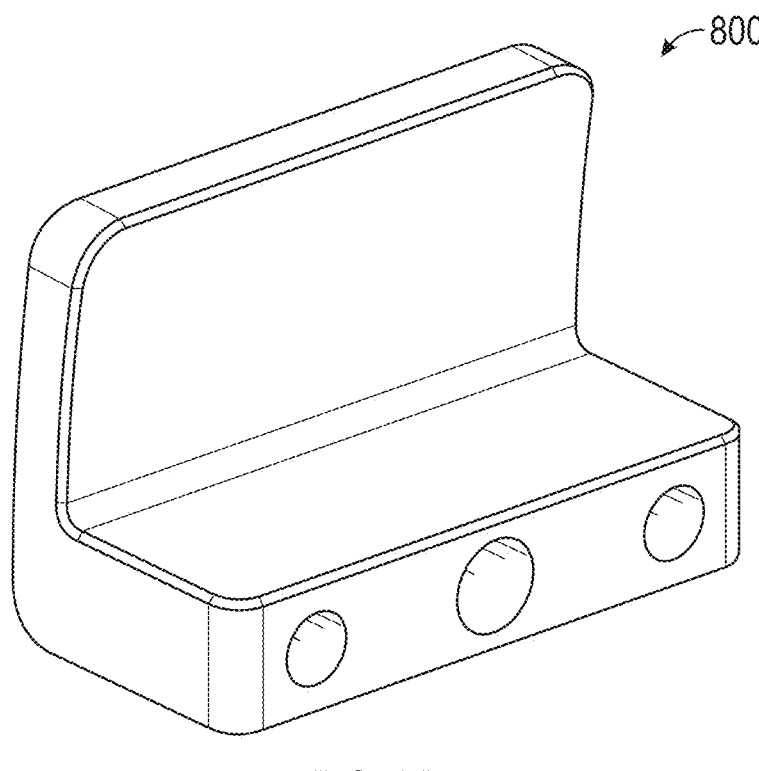
FIGS. 8A-8B show one example of a phone attachment edge that may be used with a phone attachment base such as the one shown in FIG. 7. In this example, one or more sliding pins and tightening screw (not shown) may be used to secure the base to the edge shown.
Figure 8B:
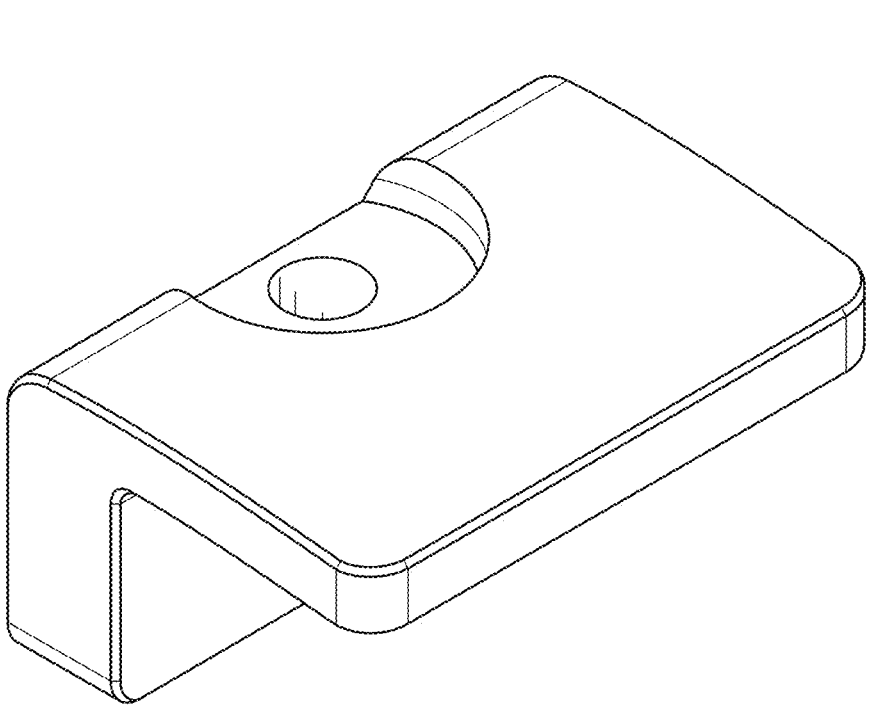

FIGS. 7 and 8A-8B illustrate portions of another releasable attachment that may be used with an apparatus similar to that shown in FIGS. 5A-5D. A first part 700, shown in FIG. 7, may clamp to a second part 800 (shown in front perspective and back perspective views in FIGS. 8A-8B), may be connected to the base projection from the tubular body and may clamp over the edge of a smartphone. The two portions 700, 800 may be coupled together by a fastener (e.g., a bolt, etc.) that may be tightened or loosened manually. The example shown in FIGS. 7 and 8A-8B may be attached on either side of the sides of a smartphone, across the back of the smartphone, without obstructing the front, and may be held in compression against the side(s) of the phone.

The smartphone dental imaging apparatuses (e.g., smartphone attachments) described herein may generally take high-quality intraoral images of patient dentition at home or clinic. The attachment-patient interface is designed to avoid excessive strain on the patient's intraoral cavity. In particular, the smartphone dental imaging apparatuses described herein provide a convenient patient interface, using a mild retractor to spreads open the patient's cheeks apart enabling nearly complete view of the patient's oral cavity. In some examples, as described above in FIGS. 1A-1C, the apparatus may include a spring-loaded smartphone clip-on portion that may provide easy attach/detach of the attachment to/from the smartphone, regardless of whether the smartphone is encased in a protective cover or not. These apparatuses may also avoid fogging of the phone lens, for example, by including vents (e.g., venetian-like vents) on the tubular body, such as on top and/or down surfaces of the tubular body, allowing venting of humidity from patient's oral cavity out of the tubular body, thus avoiding formation of fog on the smartphone lens, while blocking external light, which may result in shadows or uneven lighting.

Figure 11:
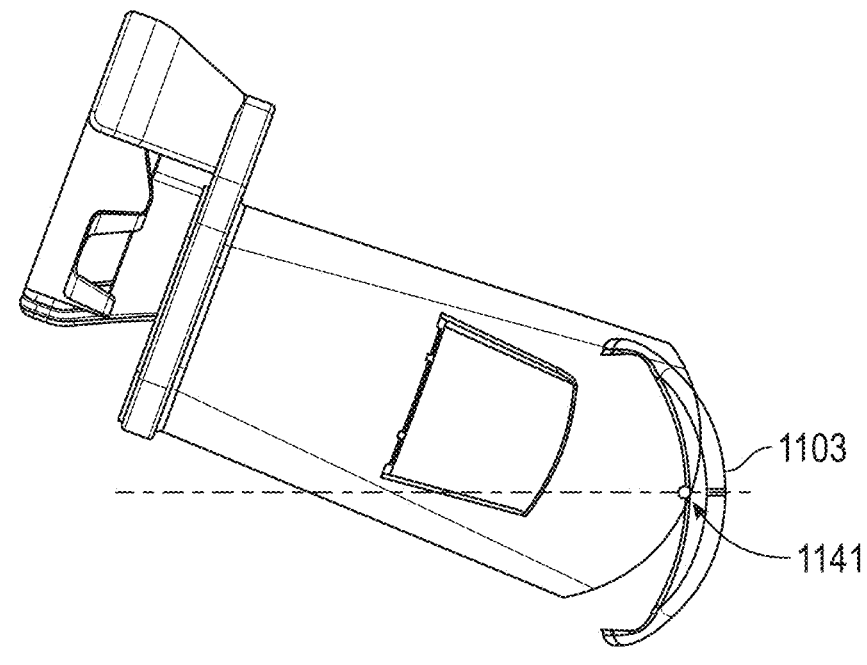
FIG. 11 shows an example of an apparatuses as described herein including a pivoting patient interface region.
Figure 12:
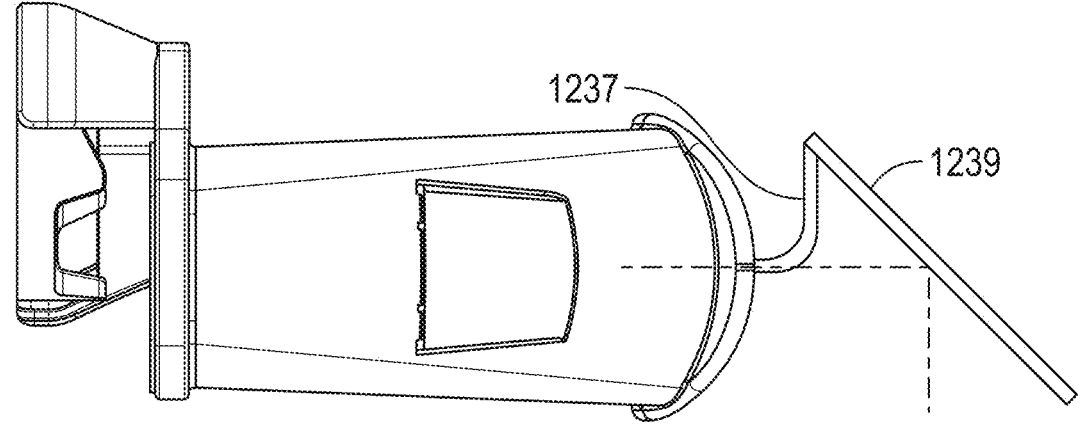
FIG. 12 shows an example of an apparatus as described herein including a mirror portion.

In some examples, these apparatuses may optionally provide relatively high quality, blur-free occlusal image taking using a tube pivot or mirror add-on, which may assist in capturing occlusal images. This is illustrated in FIGS. 11 and 12, described in greater detail below.

Figure 9:
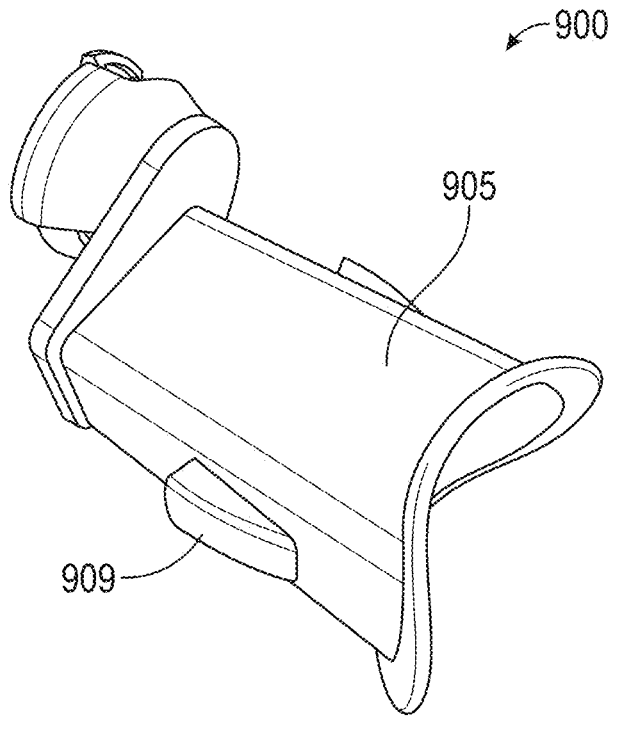
FIG. 9 illustrates another example of an apparatus as described herein.
Figure 10:
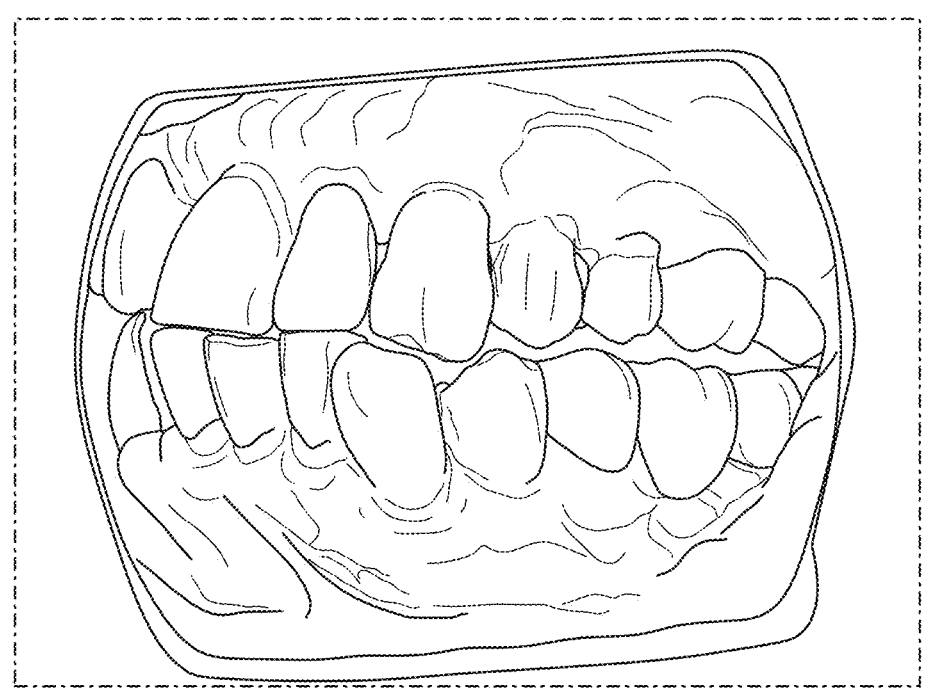
FIG. 10 is an example of an image taken with an apparatus as described herein.

As mentioned, in any of these examples, shade-free illumination may be achieved using the built-in smartphone light. In some examples, the inside of the tubular body may include a white diffusive texture resulting in shade free illumination and minimize reflections off the teeth. For example, FIG. 9 illustrates another example of an apparatus 900 that includes a tubular body 905 having a pair of vents 909 and a patient interface region. FIG. 10 illustrates one example of an image of a patient's dentition, taken with an apparatus similar to that shown in FIG. 9. The lips and cheeks are retracted by the patient interface region (not shown), so that a virtually un-occluded view may be achieved.

These apparatuses therefore include a mild cheek retractor for improved patient comfort and may be easy to attach/detach to/from smartphone. Further, these apparatuses may couple to the smartphone without blocking the smartphone screen and may prevent fogging. In addition, these apparatuses provide nearly orthogonal occlusal image taking, and shadow-free illumination. The smartphone dental imaging apparatuses may be used at home or in a clinic. The attachment-patient interface is designed to avoid excessive strain on the patient's intraoral cavity.

The tubular body may be equipped with a mild retractor for spreading open the patient's cheeks, spring-loaded smartphone clip-on mechanism, vents on either side of the tube, white diffusive texture on inside tube surfaces. In some examples, as mentioned above, the apparatus may be configured to pivot, e.g., at the tubular body or between patient interface 1103 (e.g., cheek retractor) and the tubular body, as shown in FIG. 11. In this example the patient interface 1103 includes a pivot point 1141. As shown in the example of FIG. 11, the apparatus may be used to capture an image of the side of the dentition (e.g., the patient's right side, by tiling the tube relative to the patient interface, as shown. Thus, the patient interface end may be pivoted about the long tube cross section axis allowing to tilt the tube and smartphone relative to the patient's jaw, e.g., by about 30 degrees or more for taking an occlusal image.

Any of these apparatuses may also or additionally include a flip-in flip-out fold mirror that may be attached to the first end of the tube, as shown in FIG. 12. In this example, the mirror 1239 is coupled to the tubular body, as shown, and the mirror may be held within the patient's mouth to allow imaging of the lingual side of the teeth or other region so the dentition. The mirror may be held by a mirror attachment 1237 that may project into the mouth when the patient interface is secured in the patient's mouth. These apparatuses may therefore be used to provide occlusal imaging using tube pivot and/or mirror add-on(s) to capture occlusal images.

Further, by taking plurality of photos in short burst of time these methods may include exposing each photo to different light intensity and focus. Because the apparatus may hold the dentition in a relatively fixed orientation relative to the camera of the phone, the apparatus may further assume that the camera did not move between the photos. Due to the different photo conditions, each pixel between the photos will have different attributes in terms of focus and saturation. For each pixel, its best value may be chosen from one of the images and then these values may be blended together. An example for blending could be Poisson blending. An example for value choosing criteria is choosing the pixel from the photo, which is both not, saturated (at the pixel) and has the best focus.

FIGS. 13-15 illustrate another example of an imaging apparatus as described herein, similar to that shown in FIGS. 4 and 5A-5D described above. In FIGS. 13A-13C the apparatus is configured to releasably attach to a smartphone to take orthodontic images, as described above. In this example the apparatus includes a tubular body 1305 having a central lumen 1327 extending therethrough (e.g., from a first end to a second end of the tubular body). A patient interface 1313 (e.g., mouthpiece) is formed or attached on the first end of the tubular body. In this example, the patient interface has a saddle-shaped mouth region having a rim that extends around the circumference of the first end of the tubular body. As described above, the rim is configured to fit between a patient's lips and gums.

In this example, the tubular body does no include vent covers (e.g., 109 in FIGS. 1A-1C) covering the vents, but instead, includes vent openings 1309 that are flush with the sides of the tubular body. The tubular body in this example has a wider base region 1307 at the second end than the first end (at the mouthpiece). The apparatus also includes a smartphone interface at the second end of the tubular body. The smartphone interface forms a camera opening that is configured to fit over the camera(s) of a smartphone. The smartphone interface at the base also includes a base projection 1341 that extends perpendicularly from the tubular body at the second end. The base projection in this example includes one or more (e.g., an array) of attachments 1344, shown as attachment openings, that are arranged over the length and width of the top of the base projection. The bottom of the base projection may be smooth and may be configured so as not to scratch or damage the phone, against which it may sit, as will be described below. In some examples the bottom may include a material that is soft and/or non-abrasive.

FIG. 13B shows a side view of the tubular body portion of the apparatus. In this example, the base projection 1341 extends slightly lower than the annular base 1307 region of the tubular body when the base projection is extended perpendicularly to the tubular body, as also shown in FIG. 13C. In this example, the offset distance 1355 between the base of the tubular body and the bottom of the base projection 1341 is between about 2 mm and about 15 mm (e.g., between about 2 mm and 12 mm, between about 2.5 mm and 10 mm, between about 2.5 mm and about 8 mm, between about 3 mm and about 6 mm, etc.). Thus, the tubular body may float above the surface of the smartphone when the base projection is mounted to the back of the smartphone.

The tubular body may be integrally formed with the base projection (e.g., as a single piece), or it may be formed as a separate piece. In some examples, as described below, the base projection may be hinged or movably, and in some examples, lockably, coupled to the tubular body. Thus in any of these examples the smartphone interface may include the annular base region 1307 and the base projection 1341. The annular base region may be separate from the base projection, and they may couple together.

The base projection may adjustably couple to a securement (e.g., a clip, a clamp, etc.) that secures (e.g., clamps or clips) the base projection against the back and/or side(s) of the smartphone to hold it, and therefore the tubular body, to the smartphone. The position of the tubular body relative to the one or more cameras on the back of the smartphone may be adjusted in some examples by adjusting the manner in which the base projection couples to the clamp.

FIG. 14 shows one example of a securement 1400, similar to that shown in FIG. 6. Other examples of securements are shown in FIGS. 7 and 8A-8B. In this example, the securement includes a plurality of attachment engaging members (shown in this example as a plurality of projections or posts 1447) that are arranged in an array extending from the securement. The attachment engaging members engage with the attachments (see, e.g., the attachments 1344 in FIG. 13A) on the base projection. In the example shown in FIG. 14 the attachment engaging members all extend as cylindrical posts that engage with the attachment openings, as described below. The attachment engaging members may have any appropriate cross-section, such as cylindrical, rectangular, triangular, plus-shaped, x-shaped, etc.

Figure 15A:
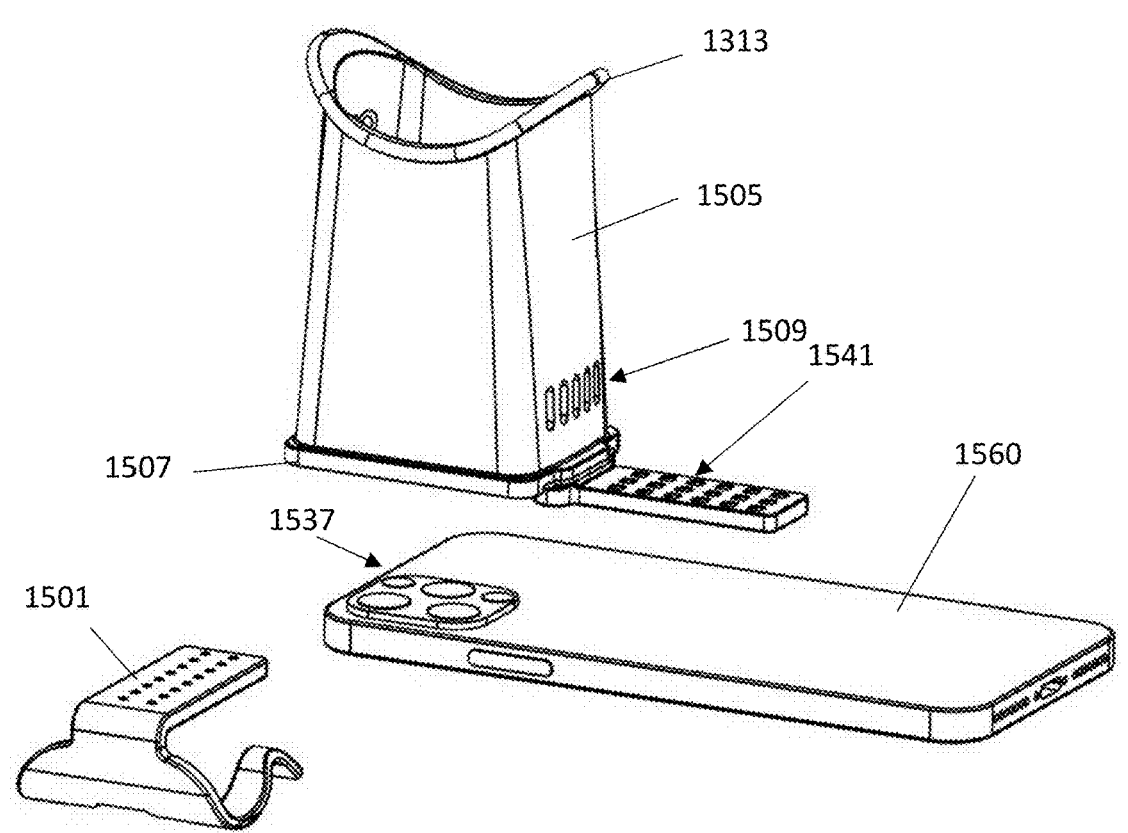
FIG. 15A is an exploded view of an apparatus for dental imaging using a smartphone as described herein. The smartphone shown in FIG. 15A does not form a part of this system.
Figure 15B:
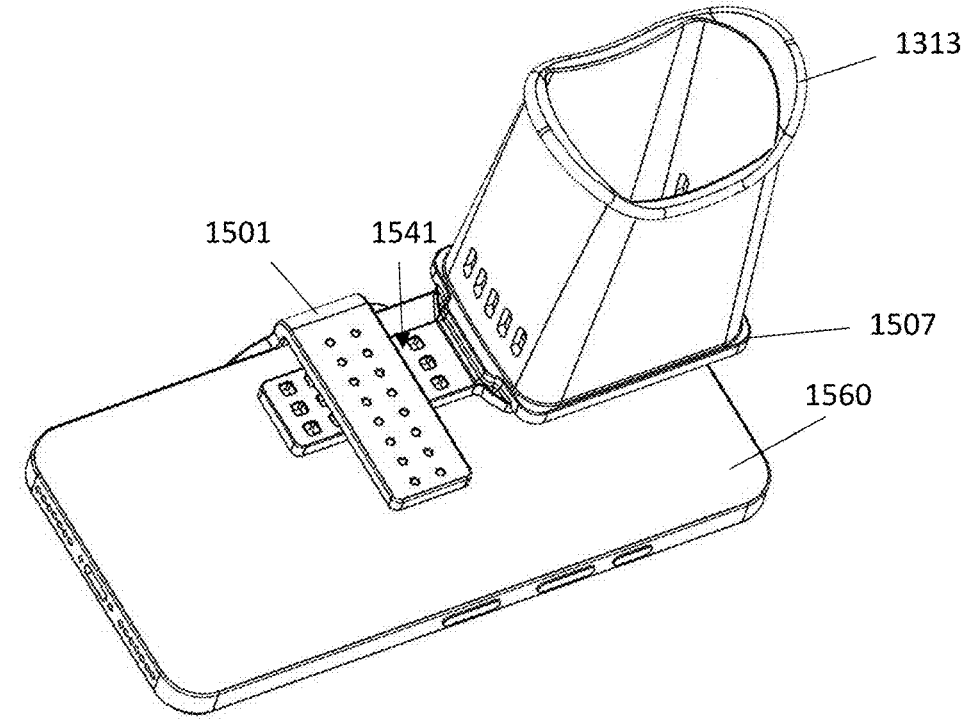
FIG. 15B illustrates one example of the apparatus of FIG. 15A assembled on a sample smartphone.

FIG. 15A shows an exploded view of one example of a system including a tubular body 1505 having a base region 1507 at the second end and a base projection 1541. The tubular body in this example also includes a plurality of vents 1509 through the tubular body near the second end (the base) to allow air flow into the tubular body, preventing fogging of the camera(s) 1537 on the smartphone 1560. Multiple air vents may be included. The air vents may be positioned on one side, two sides, threes sides, or all four sides of the elongate tubular body. The system also includes the securement 1501 configured in this example as a clip. FIG. 15B shows the system attached to the smartphone 1560, with the bottom surface of the base projection 1541 held flat against the back side of the smartphone 1560 by the securement 1501 which includes an array of attachment engaging members (not visible) that engage with attachment openings in the base projection and apply a compressive force against the base projection to hold it securely against the back of the phone, as shown. The force applied is sufficient to hold the elongate tubular body suspended above (and over) the one or more cameras while allowing the user to hold onto the phone and/or elongate tubular body with the lip region of the elongate tubular body 1513 held in the subject's mouth.

Figures 16A, 16B, 17:
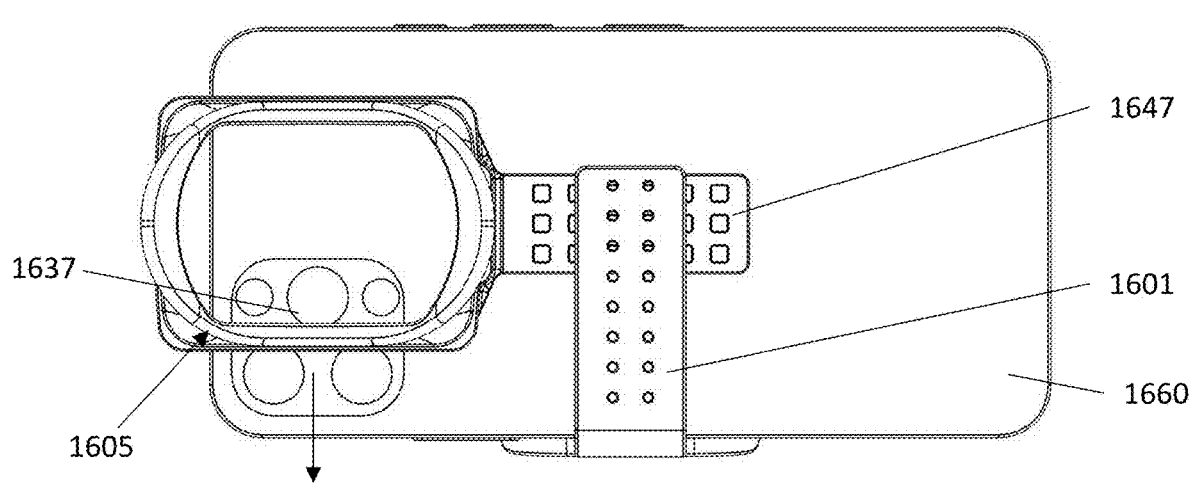
FIGS. 16A-16B illustrate adjusting the position of the elongate tubular body so that the opening of the annular base region into the channel of the elongate tubular body is aligned with the one or more camera(s) on the smartphone.
FIG. 17 shows an example of a front of a smartphone with an apparatus such as the one shown in FIG. 16B attached thereto.

The position of the elongate tubular body 1605 relative to the smartphone, and in particular, over the one or more cameras, may be adjusted by adjusting the coupling of the securement 1601 to the base projection 1647, as illustrated in FIGS. 16A-16B for one example of an apparatus applied to a smartphone. In FIG. 16A the securement 1601, shown as a clip similar to that shown in FIG. 14, engages with a first portion of the base projection 1647 so that the opening of the elongate tubular body is centered along a midline of the long axis of the back of the smartphone. In this position only one of the smartphone cameras 1637 is positioned within the elongate tubular body. The base opening of the elongate tubular body may instead be secured so that it is centered over the one or more cameras, as shown in FIG. 16B. The camera(s), light sensor(s) and flash are all within the base opening of the elongate tubular body. In both FIGS. 16A and 16B the securement may be coupled to the base projection via the plurality of attachment engaging members on the securement (e.g., clamp) engaging with the attachment openings on the base projection. Alternatively, in any of these examples the base projection may include attachment engaging members that may engage with attachment openings on the securement. In operation, the elongate tubular body 1605 may first be positioned (and/or centered) over the camera(s) and optical components on the back of the smartphone, and the securement 1601 may then be engaged with and clamped over the base projection 1647. In this manner the base opening of the elongate tubular body 1605 may be positioned virtually anywhere over the back (or in some variations, front) of the phone.

FIG. 17 shows a front view of the front of the smartphone 1660 of FIG. 16B with the apparatus clamped onto the back of the phone. Although the securement variation shown in FIGS. 14-17 is configured as a clamp that attached to the front side of the smartphone, in some examples the clamp may be configured so grip the sides of the phone but not to occlude any of the front face of the smartphone, as shown in FIGS. 18A-18B.

Figure 18A:
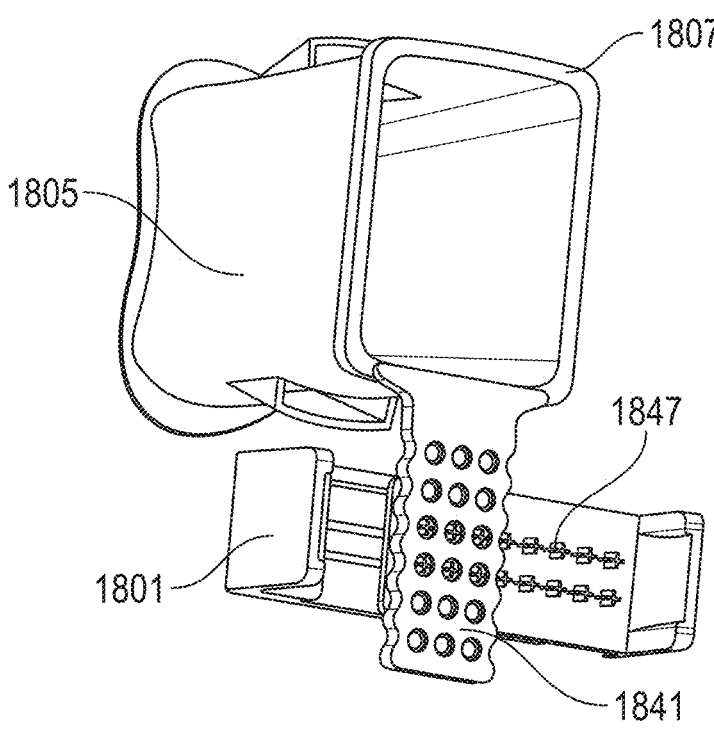
FIGS. 18A-18B illustrate another example of an apparatus as described herein, including a securement configured to secure by clamping to a smartphone without obscuring the front face of the smartphone.
Figure 18B:
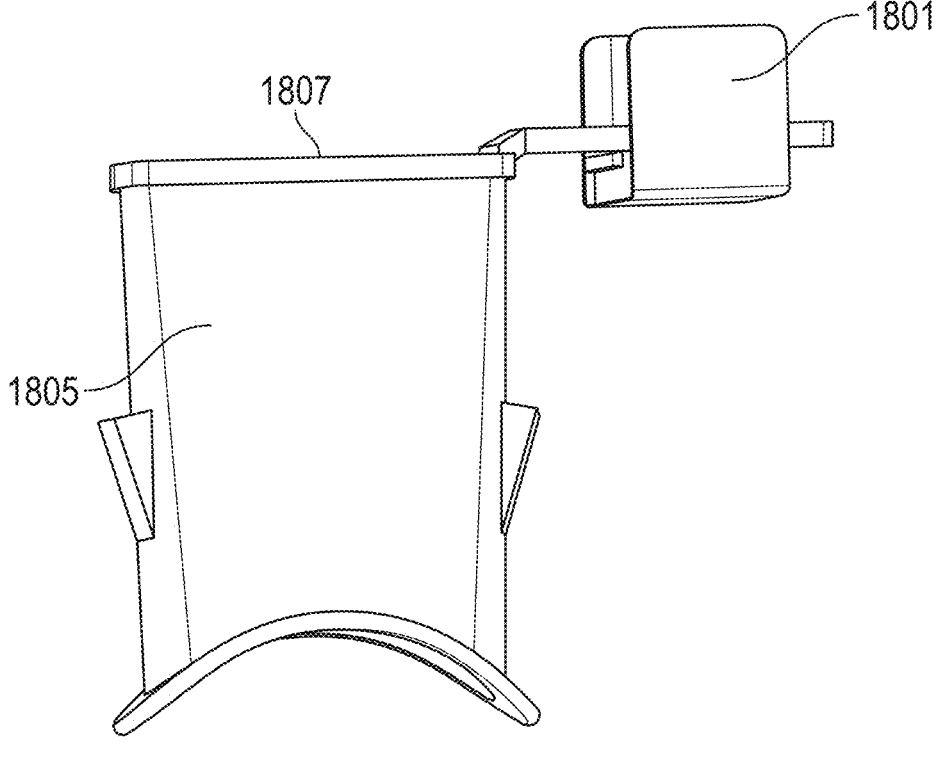
Figure 19A:
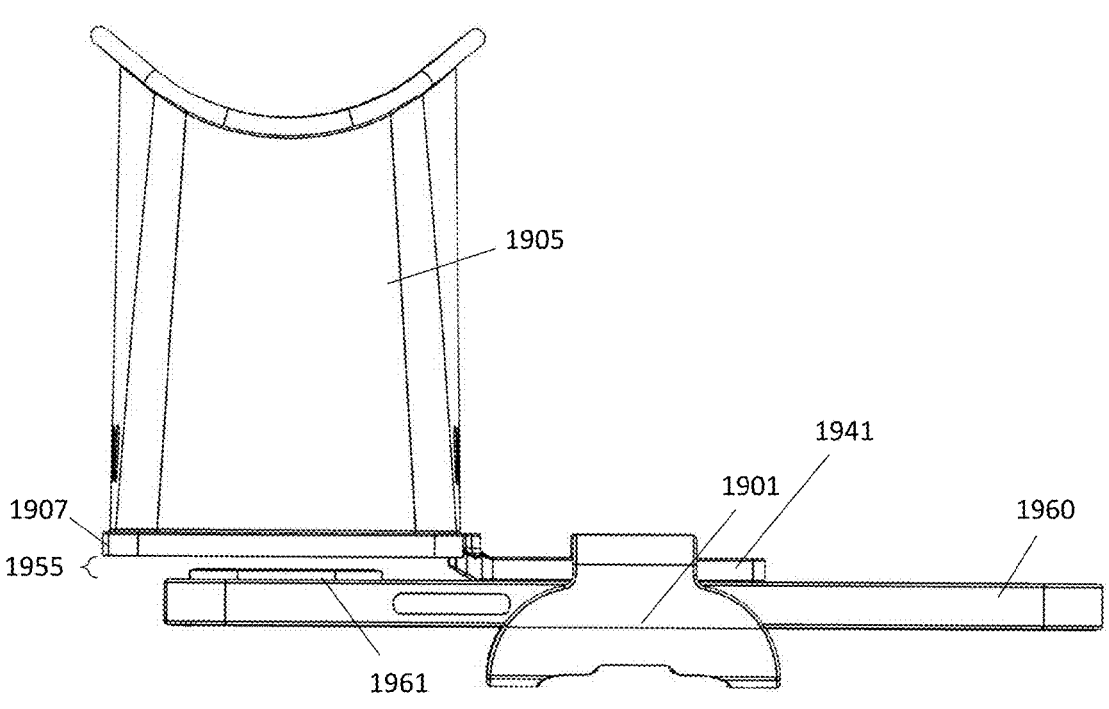
FIGS. 19A-19B show front and back views, respectively of one example of an apparatus as described herein, illustrating the separation between the base of the elongate tubular body and the back of the smartphone when the apparatus is secured to the smartphone.
Figure 19B:
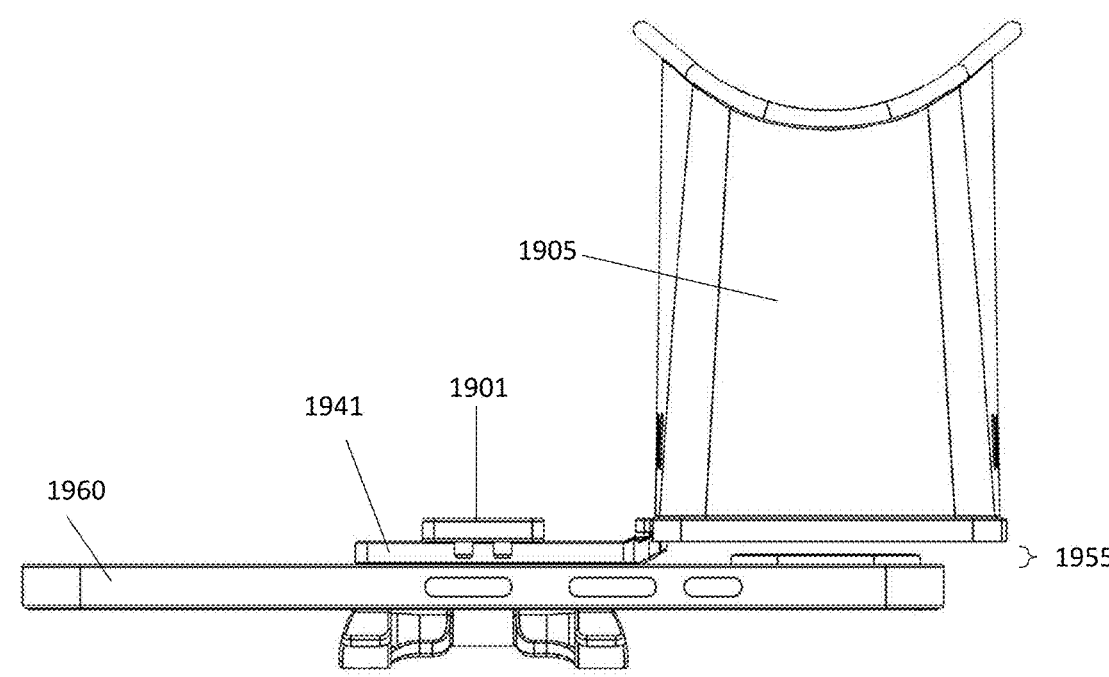

FIG. 18A shows a bottom perspective view of another example of a system as described herein, including an elongate tubular body 1805 to which a securement 1801 configured as a clamp may be engaged. The base projection 1841 extends perpendicularly to the elongate tubular body 1805 and forms a part of the smartphone interface along with the base region (annular base region) 1807. The securement 1801 is formed of two components that may slideaby engage with each other and may include a mechanism (e.g., clip, spring, screw, etc.) to secure the two together and over opposite edges of the smartphone to hold the base projection 1841 in compression against the body of the smartphone. The securement (e.g., clamp 1801) includes an array of projecting members 1847 extending from the securement and configured to engage engagement openings on the base projection. FIG. 18B shows a side view of the system shown in FIG. 18A. In any of these examples described herein, when the system is attached to a smartphone, the annular base region 1807 at the second end of the elongate tubular body 1805 may be separated from the back of the phone, including the region peripheral to the camera (or camera components). Instead, the elongate tubular body may be cantilevered over the camera(s)/camera components. This may allow the apparatus to be used with a variety of different phones having different configurations. It may also provide ventilation (or additional ventilation) across the camera(s) to prevent fogging of the camera(s). This is illustrated in FIGS. 19A and 19B. For example, in FIG. 19A the annular base region 1907 of the elongate tubular body 1905 is suspended over the back of the smartphone 1960, including the slightly protruding camera and optics assembly 1961 of the smartphone 1960. As discussed above, the base region 1907 of the elongate tubular body 1905 may be separated from the back of the smartphone 1960 by appropriate distance 1955, such as between about 2 mm and about 20 mm (e.g., between about 2 mm and about 15 mm, between about 2 mm and about 12 mm, between about 2.5 mm and about 10 mm, between about 2 mm and about 6 mm, etc.). The base projection 1941 may be lower than the annular base region 1907 so that the annular base region and the elongate tubular body is cantilevered above the camera on the back of the smartphone when the base projection 1941 is clamped against the back of the smartphone by the securement 1901 (shown as a clip in FIGS. 19A-19B, similar to that shown in FIG. 14). In any of these apparatuses the base projection may be referred to as a leg or tab.

Figures 20A, 20B, 20C, 20D:
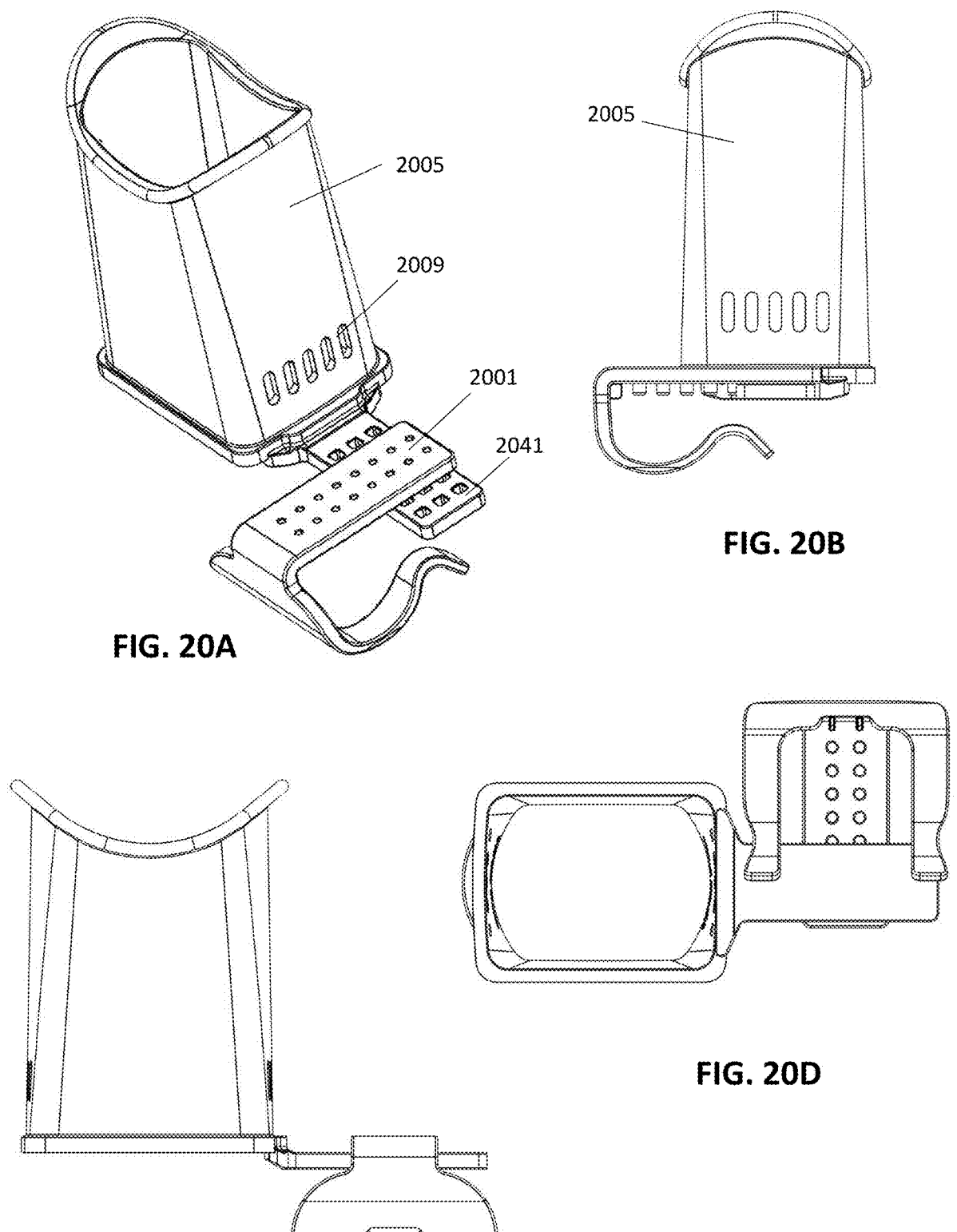
FIGS. 20A-20D show side perspective, side, front and bottom views, respectively of one example of a system as described herein.

FIGS. 20A-20D illustrate an apparatus (e.g., system) as described herein, similar to that shown in FIGS. 19A-19B. FIG. 20A shows a perspective view of the apparatus with the securement 2001 coupled with the base projection 2041 of the smartphone interface that is coupled (in this example, integrally formed) with the elongate tubular body 2005. The tubular body includes five vent openings near the base of the wall. FIGS. 20B, 20C and 20D show right side, front and bottom views, respectively of the apparatus of FIG. 20A.

In some examples the securement portion may act as both a clamp and a clip; for example, the securement may couple to the base projection extending from the annular base region the elongate cylindrical body and may clamp to the sides of the phone as well as to the back, rather than just the sides or just the back. For example, a securement may include two (or more) parts that move (to clamp/unclamp) relative each other as well as a clip portion that may extend over the front of the phone at least partially. In any of the clamping securements described herein, the movement of the securement may be a sliding movement and may be biased closed, e.g., by a spring. Alternatively in some examples the movement may be locked or unlocked by engaging/disengaging a locking member (screw, cam, etc.). One of the two securement parts may include a clip portion.

In some examples the base projection (or tab or leg) may be hinged relative to the elongate tubular body, and in particular, relative to the annular base region of the elongate tubular body. This may allow the base projection to fold up against the side of the elongate tubular body for compact storage and/or packaging. The base projection may be a stiff member that is hinged so that it may fold up in a compact, closed configuration, but may unfold out perpendicular to the elongate tubular body. The base projection may be configured to lock in this perpendicular configuration, so that it may not extend further than the plane of the annular base region and may (in some examples) be held fixed in this configuration.

Figure 21A:
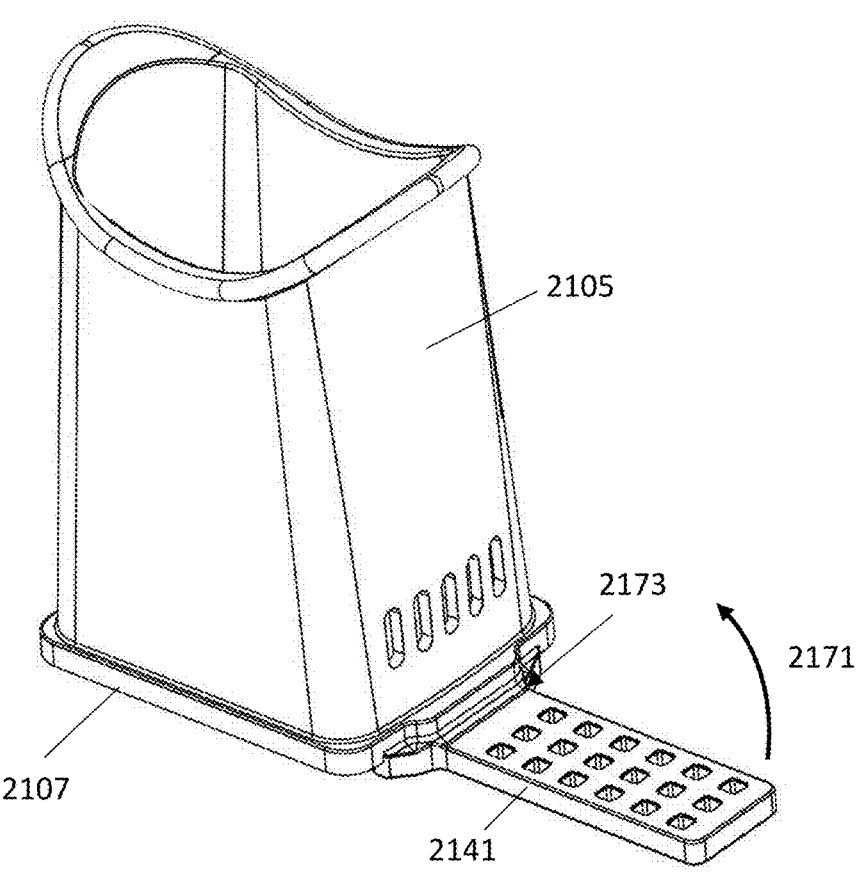
FIGS. 21A-21B illustrate an example of an apparatus in which the base projection (e.g., tab or leg) is hinged to the elongate tubular body so that it may be folded relative to the elongate tubular body.
Figure 21B:
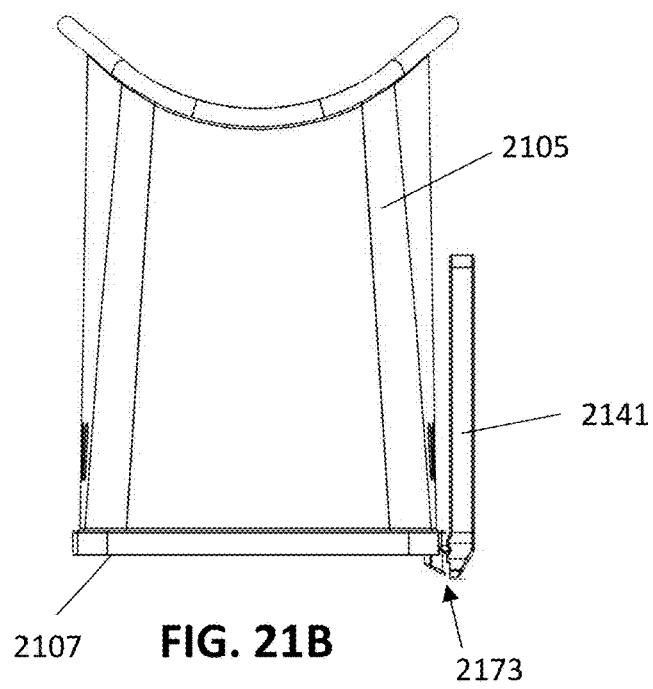

For example, FIG. 21A illustrates a portion of an apparatus in which the base projection (tab) 2141 is hinged 2173 so that it may fold up 2171 against the outer side of the elongate tubular body 2105. The hinge may be configured so that it cannot fold down further than parallel with the annular base region 2107. FIG. 21B illustrates this portion of the apparatus in the collapsed, folded configuration. In FIG. 21B the base projection 2141 is folded upwards against the elongate tubular body 2105 into a compact configuration that may be more easily packaged and transported. Before use, the apparatus may be deployed by folding down the base projection 2141 so that it is perpendicular to the elongate tubular body 2105 as shown. The base projection may then be engaged with a securement and held against the outside of the smartphone, as described above.

Another example of an apparatus (e.g., a smartphone imaging apparatus) is shown in FIGS. 22A-22E, 23A-23B, 24A-24A, 25A-25B, 26A-26B and 27A-27B. As shown in FIGS. 22A-22E, in this example the apparatus (e.g., system) includes a tubular body 2205 having a central lumen extending therethrough, from a first end to a second end. In this example the tubular body includes a vent 2209. The tubular body is tapered and includes a patient interface on the first end of the tubular body, having a flanged rim 2213, 2213' configured to fit between a patient's lips and gums. In this example the flanged rim is not continuous, but extends on opposite sides of the first end, at an angle relative to the long axis of the tubular body. The first end also include two cut-down regions 2283 on opposite sides of the first end and between the flanged rims 2213, 2213'. The second end of the tubular body connects to a smartphone interface including a frame 2258 forming an annular base region that includes an opening into the central lumen that is configured to fit over one or more cameras of a smartphone. The frame also includes (or is coupled to) a base projection 2241 that extends parallel to the annular base region, but is laterally offset from the annular base region. The apparatus also includes a securement 2201 configured to clamp or clip to one or more sides of the smartphone to hold the base projection 2241 against a back of the smartphone. The securement 2201 includes a plate including an array of attachments 2247 configured to engage complementary attachments (e.g., openings 2344 in FIG. 23A) on the base projection. The annular base region is configured to cantilever over the back of the smartphone when the base projection is held against the back of the smartphone by the securement.

In FIGS. 22A-22E the smartphone interface includes the frame 2258 coupled to the second end of the tubular body to form the camera opening. The base projection 2241 is integral with or coupled to the frame 2258. The frame may couple to the second end of the tubular body 2205 by one or more connectors 2288. The connectors may be snap fit or friction fit connectors. In FIGS. 22A-22E the connectors 2288 on the tubular body are configured to mate with complementary connectors on the frame. For example, the connectors 2288 on the tubular body may include projections (e.g., tabs) that project out from the body. The complementary connectors 2289 on the frame may include openings, cavities or channels into which the projections may engage. The arrangement of connectors and complementary connectors (e.g., male/female connectors) may be reversed (e.g., female/male). The connection between these connectors is releasable.

Figure 22A:
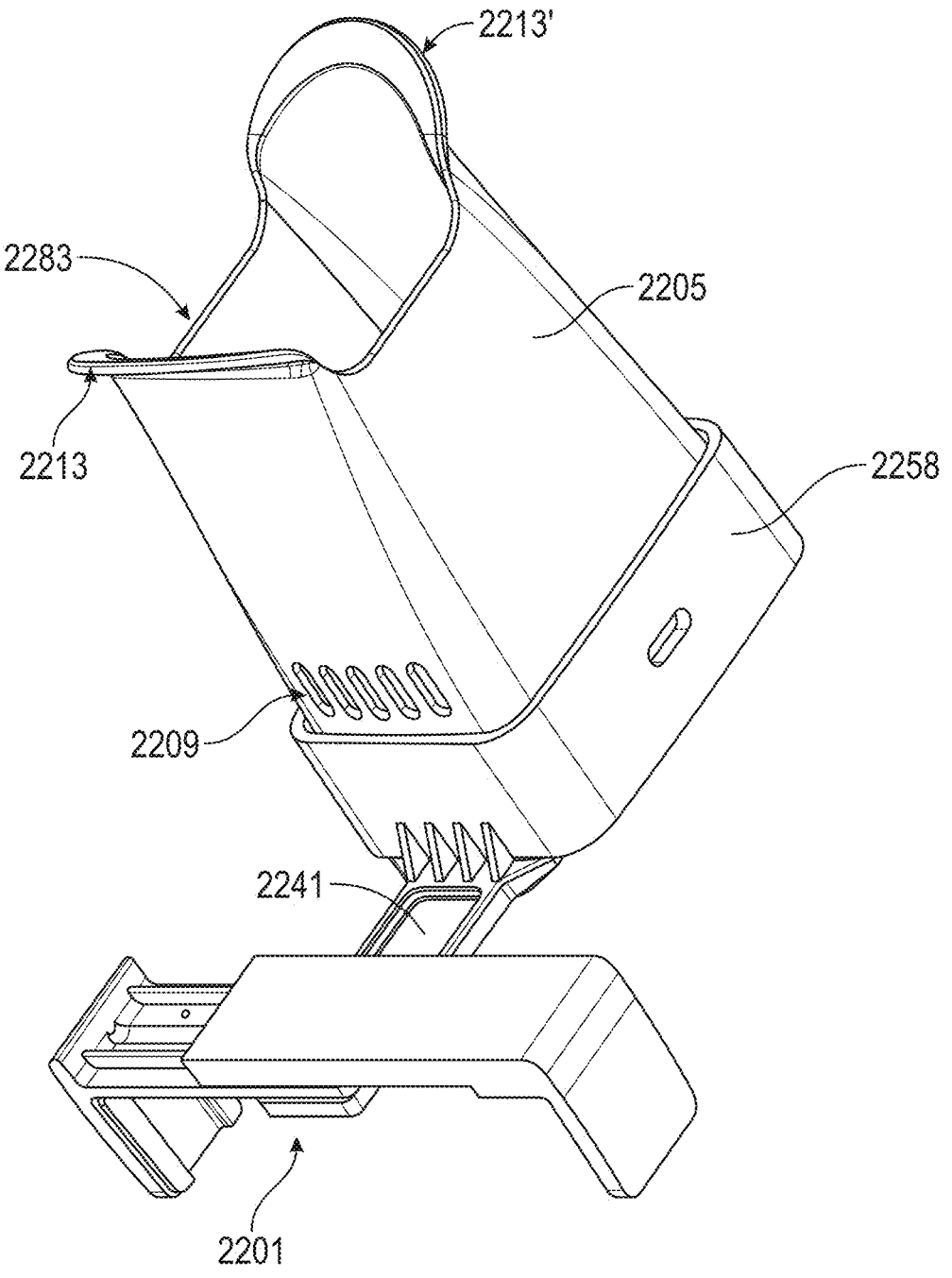
FIG. 22A-22E illustrate an example of a smartphone imaging apparatus as described herein.
Figure 22B:
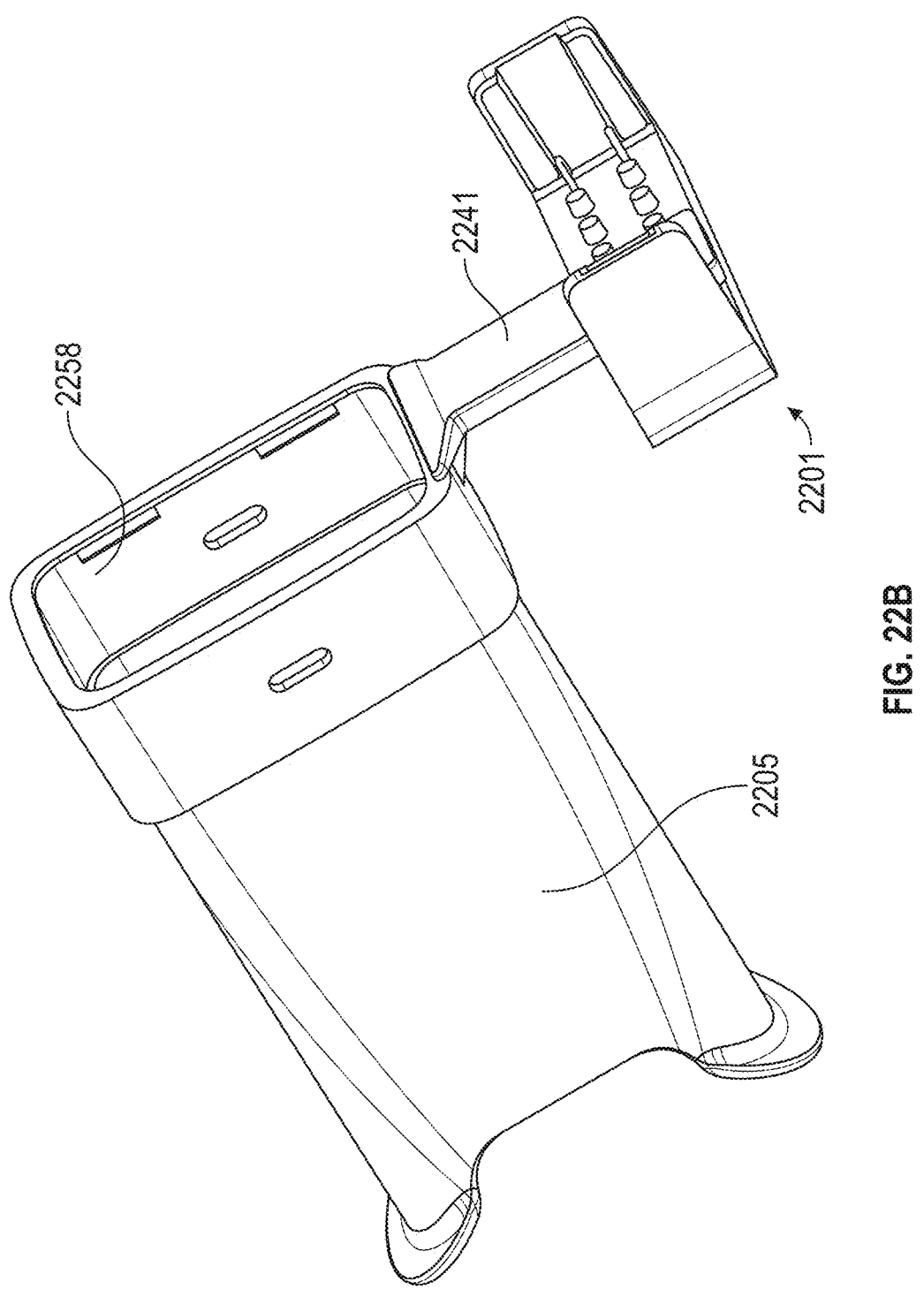
Figure 22C:
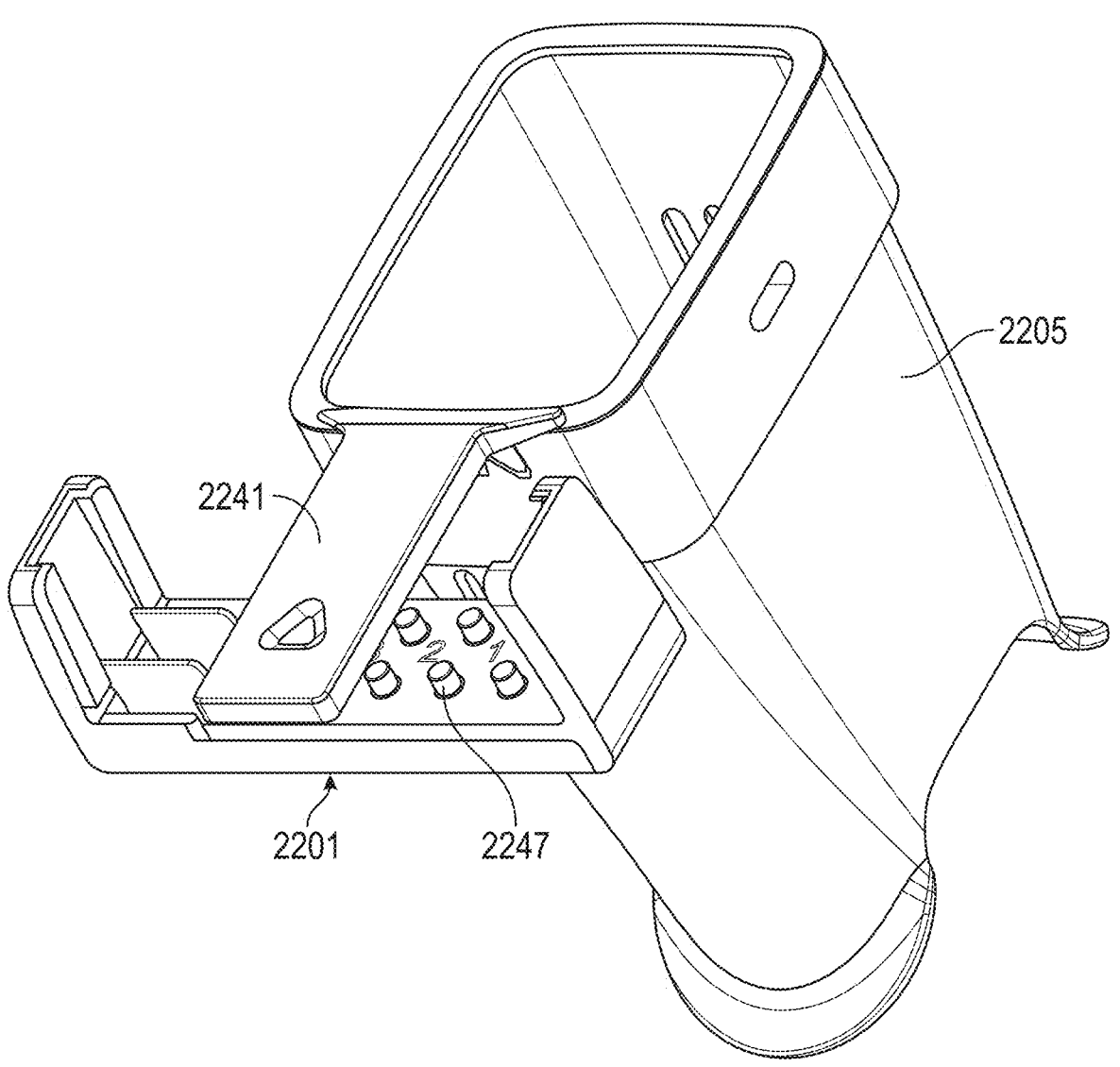
Figure 22D:
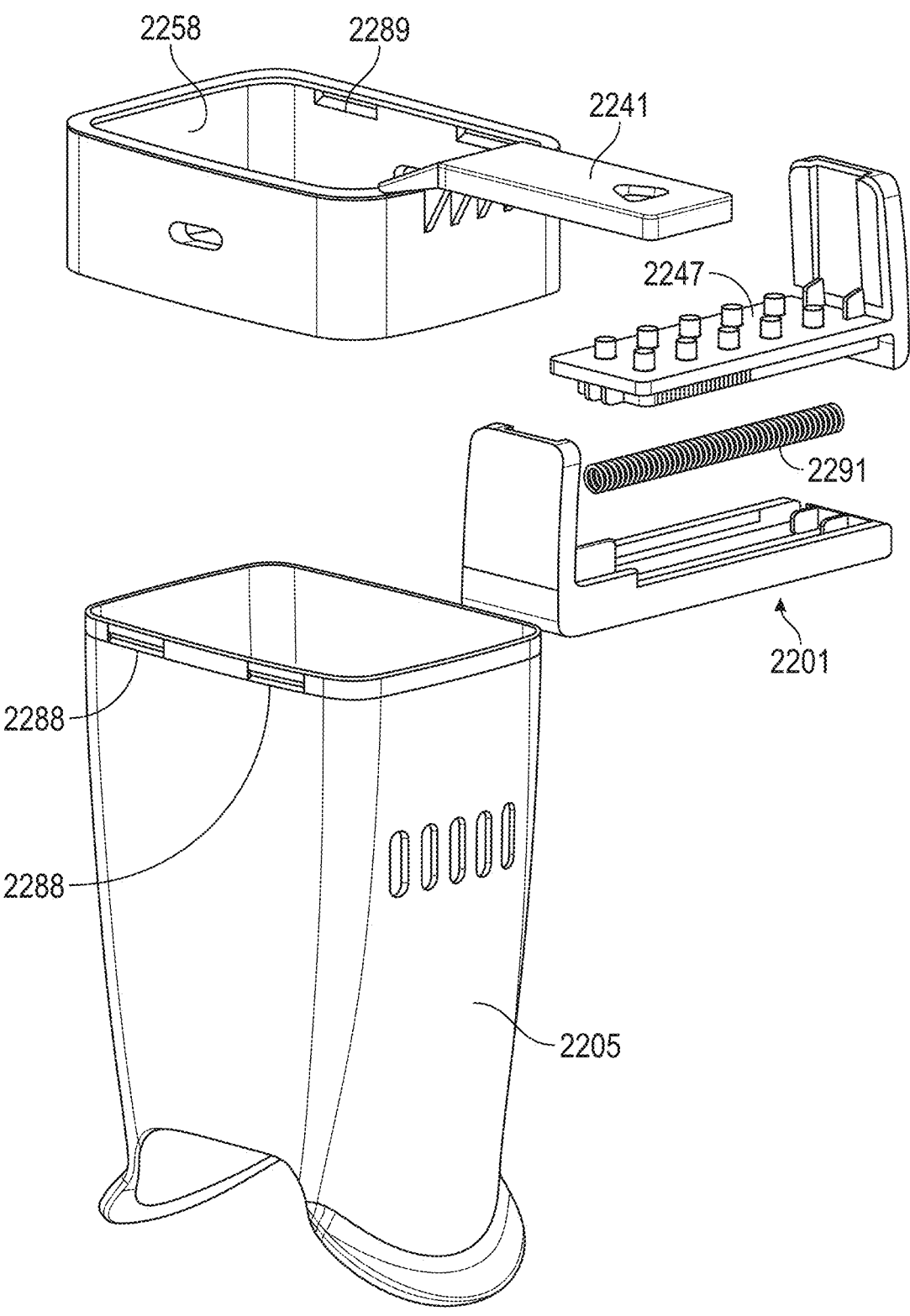
Figure 22E:
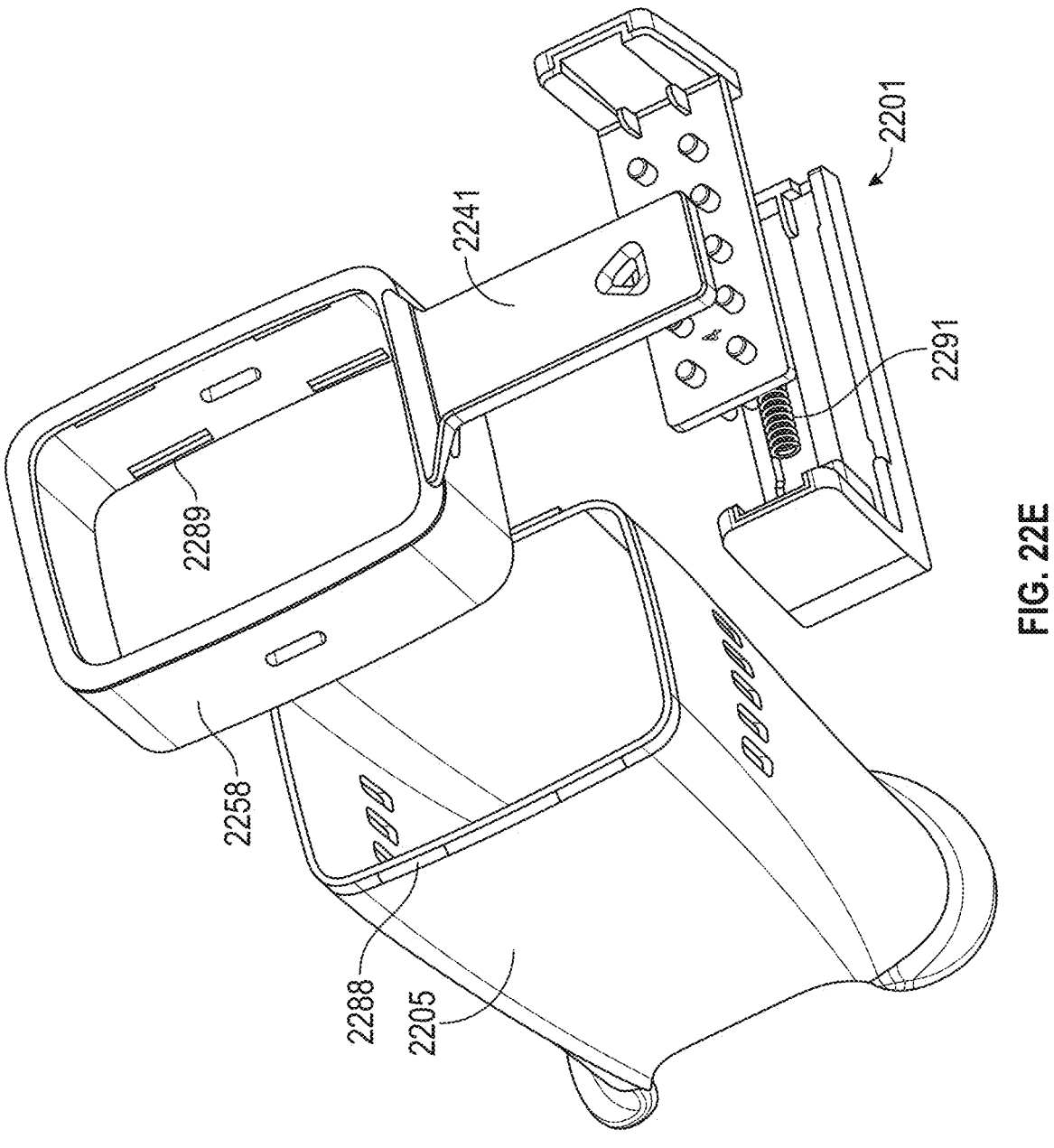

As shown in the exploded views of FIGS. 22D and 22E, the securement 2201 may include a clamp or clasp having two or more parts, including a bias 2291(e.g., spring) biased to pull the two L-shaped parts forming the clamp or clasp toward each other to hold the phone securely against the base projection. When the apparatus is secured to the phone, as described above, the annular base region is cantilevered over the back of the phone (e.g., between about 2 mm-15 mm over the back of a smartphone).

Figure 23A:
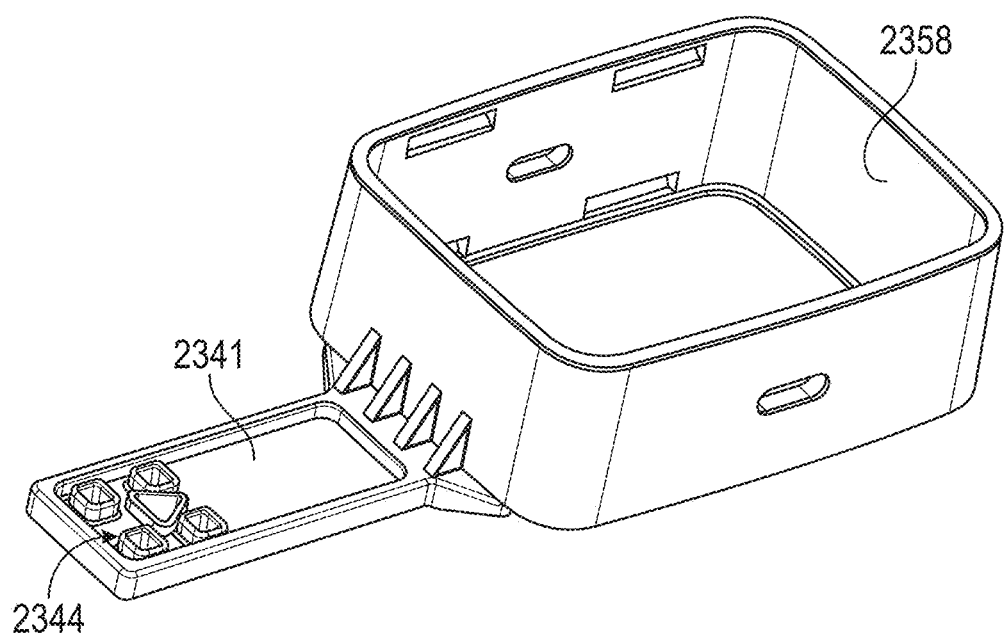
FIGS. 23A-23B show an example of a fame portion of a smartphone imaging apparatus.
Figure 23B:
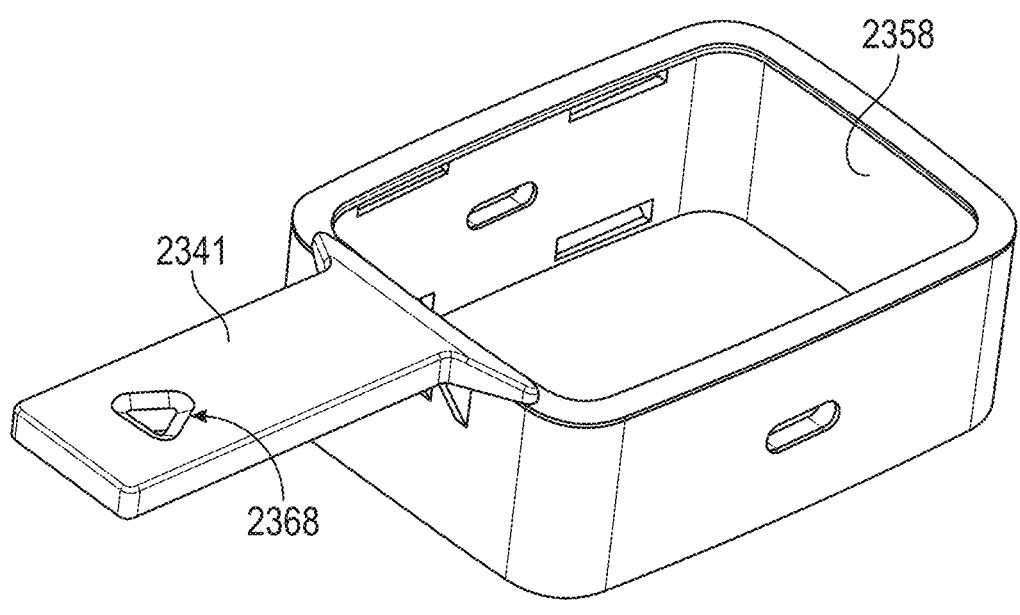
Figure 24A:
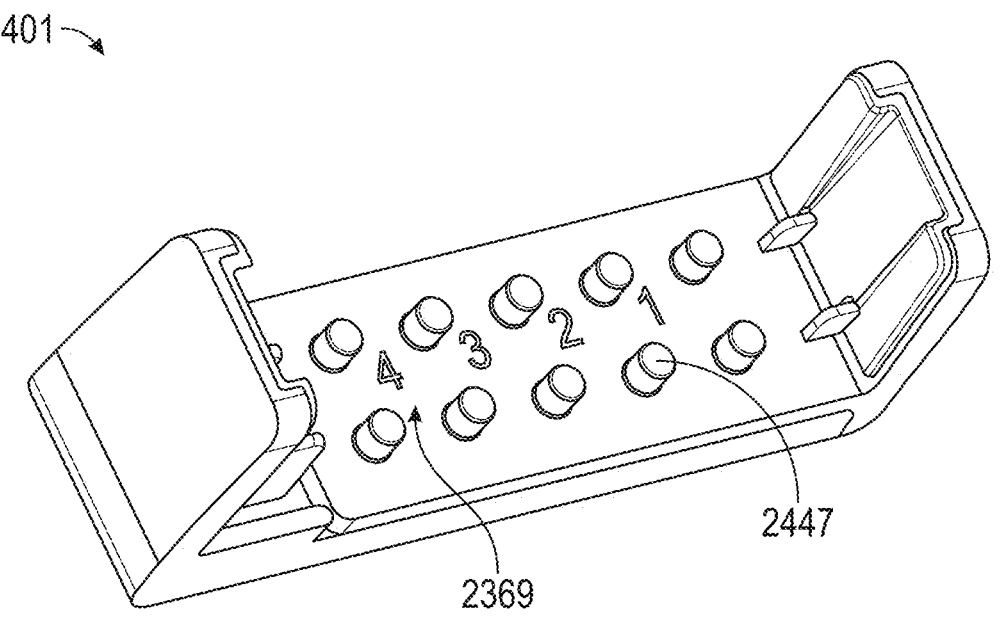
FIGS. 24A and 24B illustrate examples of securement portion of a smartphone imaging apparatus as described herein.
Figure 24B:
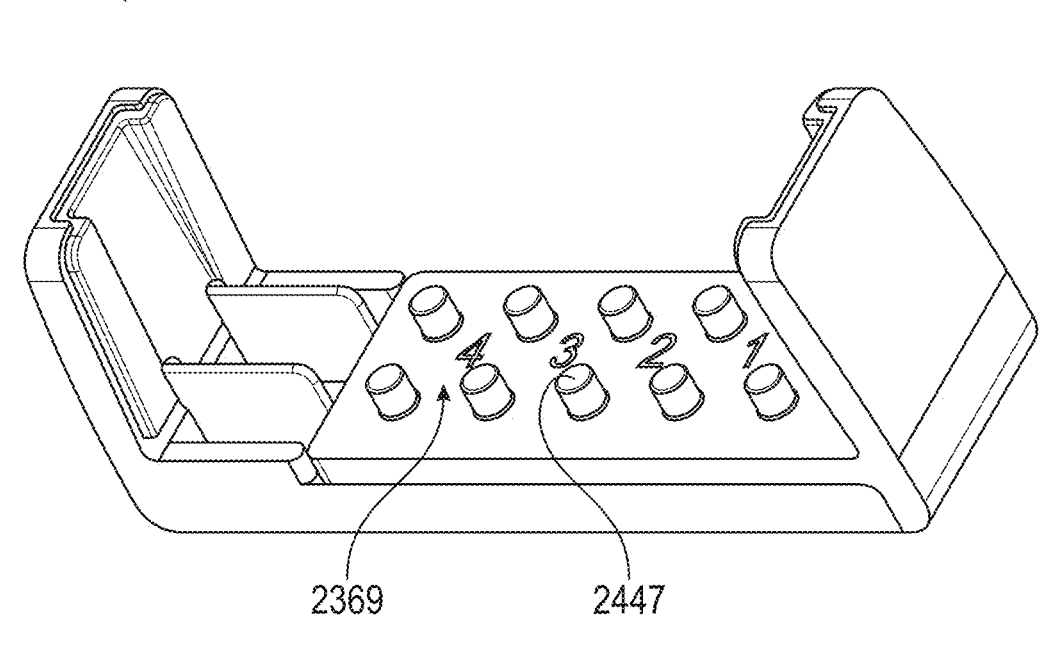

FIGS. 23A and 23B illustrate examples of the frame 2358 including the integral base projection 2341. The base projection also includes an array of openings 2344 into which, as shown in FIGS. 24A-24B, attachments (e.g., posts 2447) on the clamp portion of the securement 2401 may couple to secure the apparatus to the phone. In FIGS. 24A-24B the clasp or clamp forming the securement 2401 include labeled (e.g., numbered) markings 2369 that may be visualized through a window 2368 on the base projection to indicate the position of the frame and therefore the tubular body relative to the clamp and therefore the phone to which it is attached.

Figures 25A, 25B:
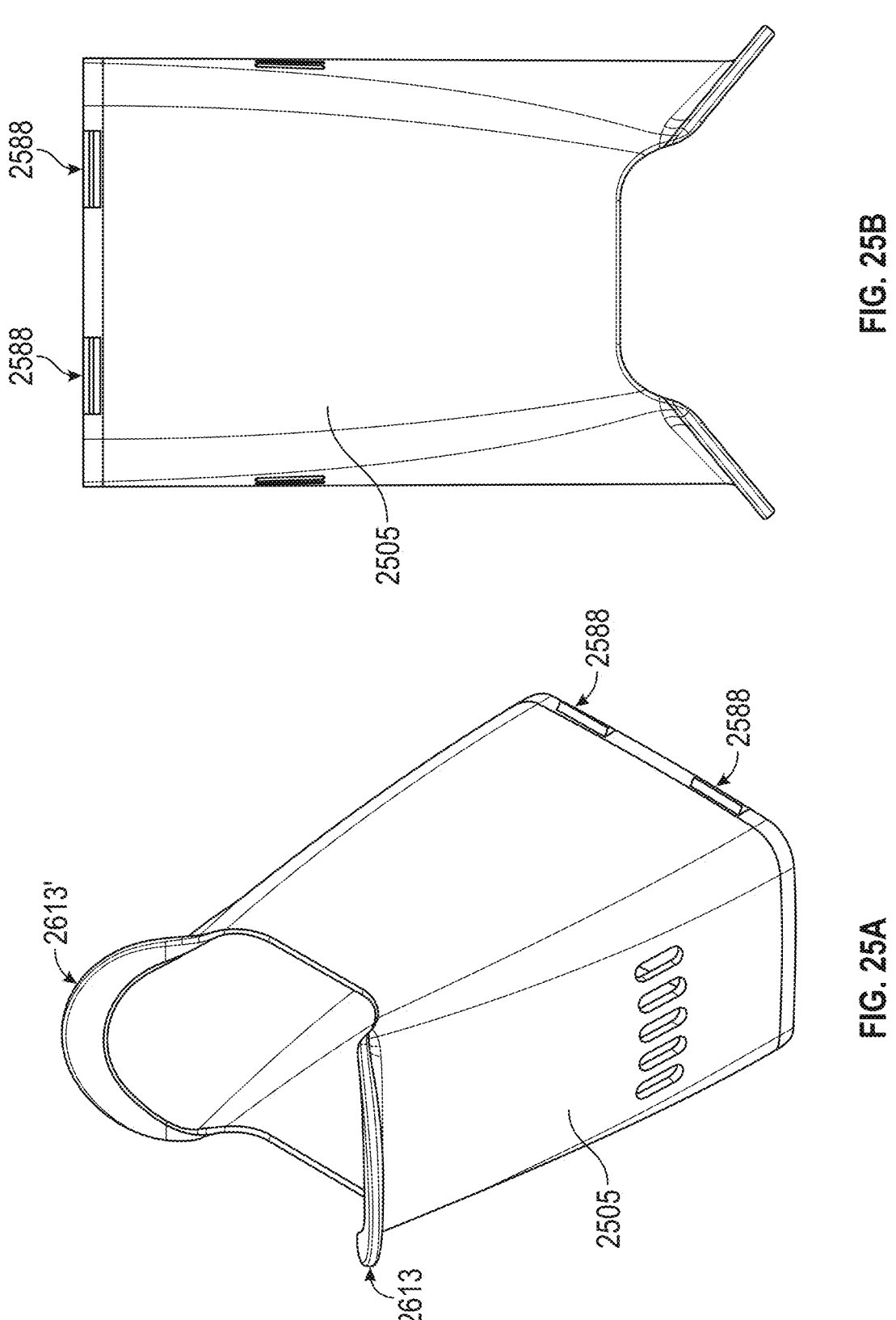
FIGS. 25A-25B show top perspective and side views, respectively of a tube portion of a smartphone imaging apparatus as described herein.
Figures 26A, 26B:
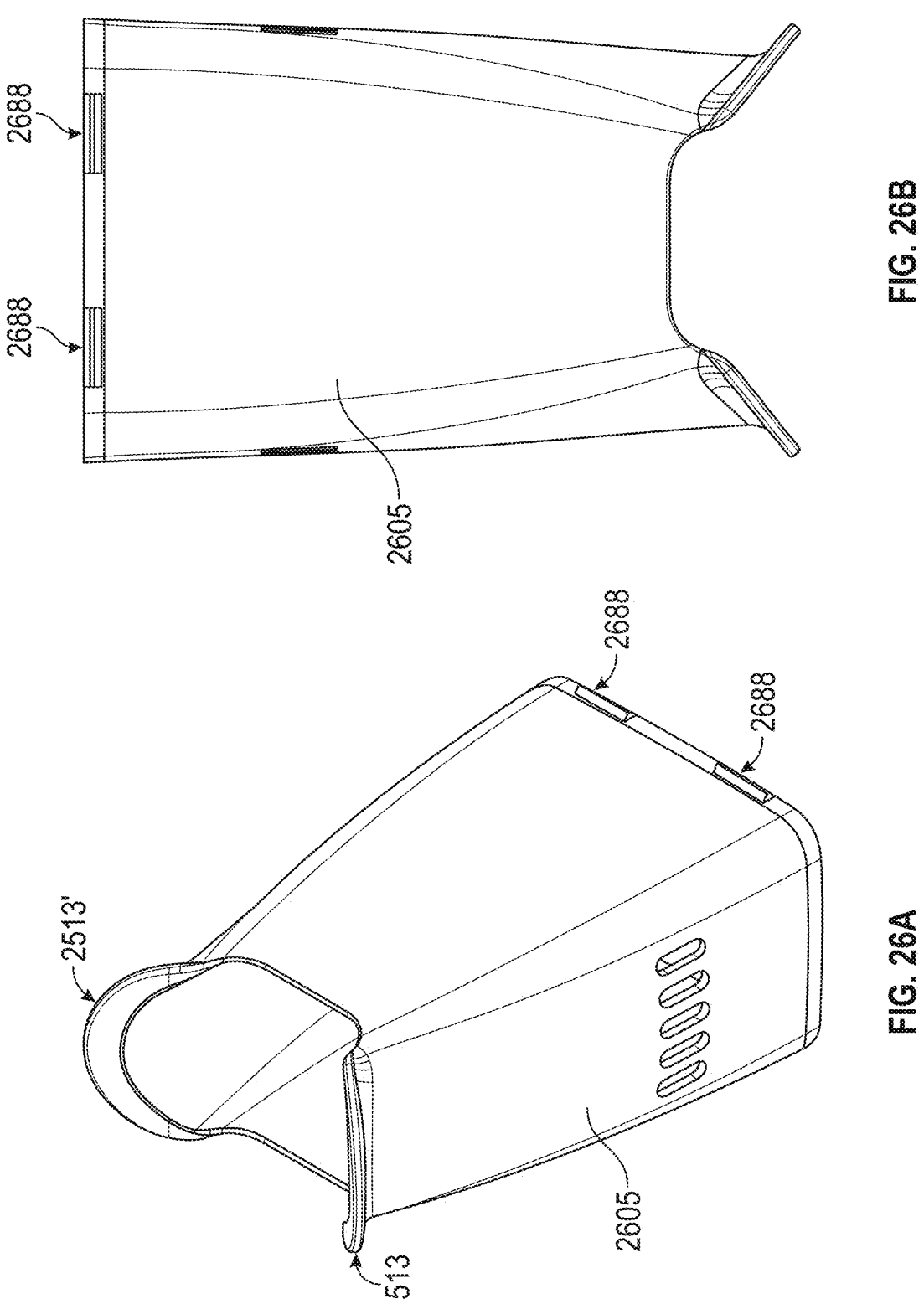
FIGS. 26A-26B show top perspective and side views, respectively of a tube portion of a smartphone imaging apparatus similar to that shown in FIGS. 25A-25B but sized for a child.

Any appropriately sized tubular body may be used, including sizes specific for adults or children. For example, FIGS. 25A-25B show a tubular body 2505 that is sized for an adult, and includes flanged rim regions 2613, 2613' and attachments 2588 for attaching to a frame, as described above in reference to FIGS. 22A-22E. For comparison, FIGS. 26A-26B show a tubular body 2605 that is sized for a child, and includes flanged rim regions 2513, 2513' that are slightly smaller and attachments 2688 for attaching to a frame that are the same size, so that both child and adult size tubes may be used with the same frame and securements, as described above. The tubular body in the child size is slightly more tapered.

Figures 27A, 27B:
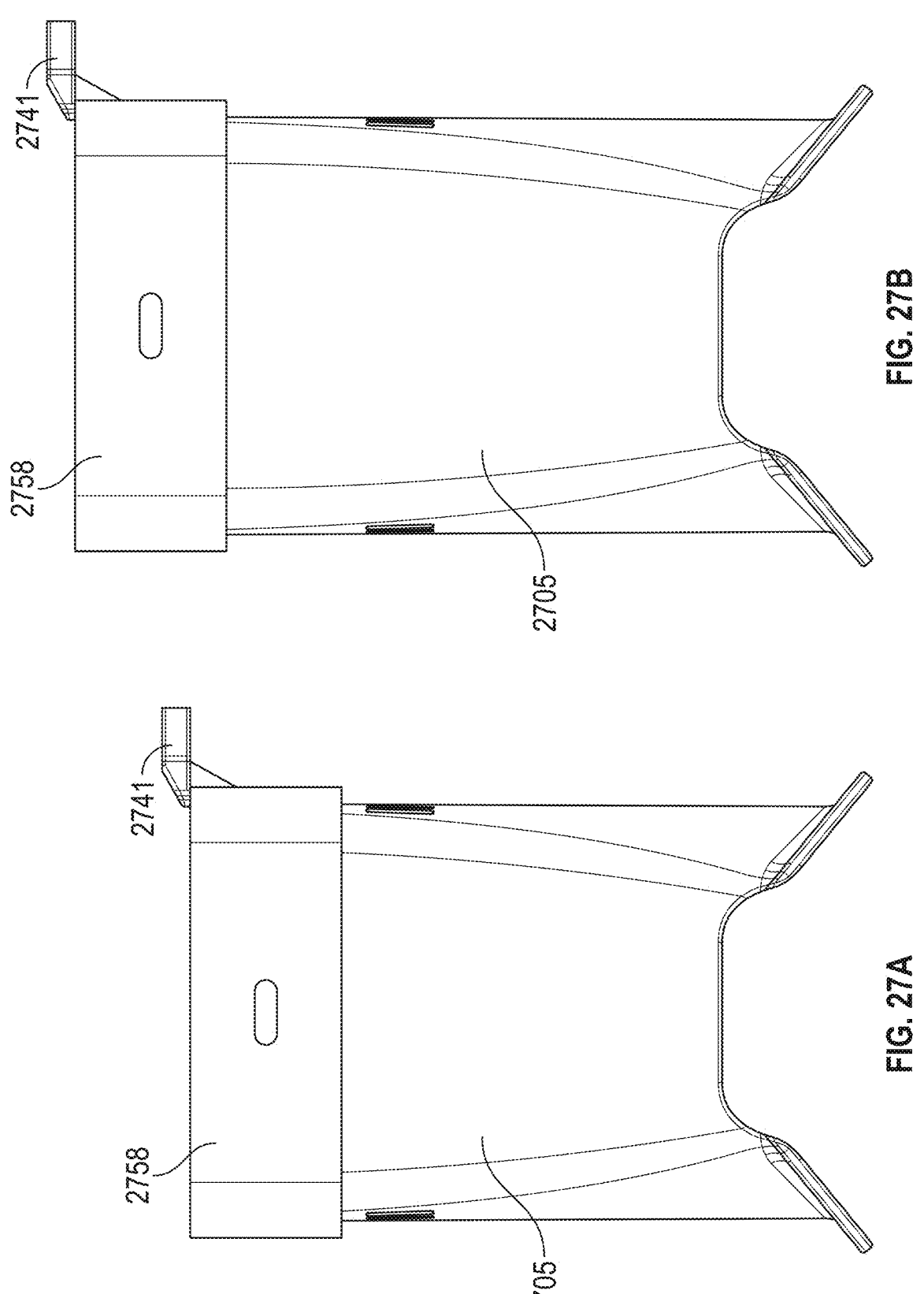
FIGS. 27A-27B show a smartphone imaging apparatus as described herein with alternative connections to the frame portion of the apparatus to extend the length of the device.

The length (focal length) of these apparatuses may be adjusted or selected, as shown by FIGS. 27A and 27B. In this case, the apparatus may have two lengths, a shorter length (FIG. 27A) and a longer length (FIG. 27B) despite having the same tubular body 2705. The same apparatus may select between these lengths depending on which internal complementary connectors within the frame 2758 that mate with connectors on the tubular body. Longer sizes may be selected by engaging connectors near the end of the frame furthest from the base projection 2741. Shorter sizes may be selected by engaging connectors near the end of the frame that is closer to the base projection 2741.

In general, the apparatuses described herein may be completely passive, e.g., without any electronics or powered components. Alternatively any of these apparatuses may include one or more active components, such as lighting (e.g., LEDs). For example, one or more of visible light, florescence, UV, near-IR, blue, and/or other wavelengths may be provided. Any of these apparatuses may also include one or more optical components, even passive optical components, such as lenses, mirrors, or the like. In some variations one or more of the inner walls of the elongate tubular body may include mirrors, providing a kaleidoscope effect providing numerous (simultaneous) angles of images. In some examples the inside of the elongate tubular body may include one or more targets or calibration markings for use in calibrating the smartphone camera(s).

In use, in some cases these apparatuses may be used as part of a method in which patient take images of dentition and soft tissue (gums, tongue, cheeks) and upload to a remote site (e.g., cloud, including a remote processor). Manual (e.g., Doctor) or automated (e.g., machine learning algorithm) may then be used to detect issues which require dental follow up such as plaque, caries, gum recession/inflammation, chipped teeth, bruxism, damages restoration, etc. In general, these methods and apparatuses may be used for dental office record taking.

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System.

As used herein, the use of the terms "orthodontic aligner", "aligner", or "dental aligner" is synonymous with the use of the terms "appliance" and "dental appliance" in terms of dental applications. For purposes of clarity, examples are hereinafter described within the context of the use and application of appliances, and more specifically "dental appliances."

As used herein, a "subject" (or alternatively and equivalently, an "individual") may be any subject (e.g., human, non-human, adult, child, etc.) and may be alternatively and may be a patient, a subject under treatment, or the like. A subject may be a medical patient. An individual or a subject may include a person who receives orthodontic treatment, including orthodontic treatment with a series of orthodontic aligners.

The apparatuses and/or methods (e.g., systems, devices, etc.) described below can be used with and/or integrated into an orthodontic treatment plan. The apparatuses and/or methods described herein may include comparison of the images taken with the apparatus to a three-dimensional model, such as a 3D mesh model or a 3D point cloud.

The methods described herein may be performed by an apparatus, such as a data processing system, which may include hardware, software, and/or firmware for performing many of these steps described above.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous examples, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the individual matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

What is claimed is:

1. A system, the system comprising:
a tubular body having a central lumen extending therethrough, from a first end to a second end;
a patient interface on the first end of the tubular body, wherein the patient interface comprises a saddle-shaped mouth region having a rim extending around at least a portion of the circumference of the first end of the tubular body and configured to fit between a patient's lips and gums; and
a smartphone interface at the second end of the tubular body, wherein the smartphone interface comprises:
a camera opening configured to fit over a camera of a smartphone;
a base projection extending perpendicularly from the tubular body at the second end and one or more openings disposed on the base projection; and
a clip or clamp configured to clamp or clip to one or more sides of the smartphone, the clip or clamp further comprising an array of projecting members, wherein the clip or clamp is configured to attach to and detach from the base projection through a subset of the array of projecting members and one or more openings within the base projection, and wherein the clip or clamp is configured to retain the smartphone at a location corresponding to a position at which the base projection is attached to the clip or clamp.

2. The system of claim 1, wherein the rim comprises a pair of sections on opposite sides of the first end that flare outwards to form the saddle shape.

3. The system of claim 2, wherein a region of the first end of the tubular body between the pair of sections does not include a flange.

4. The system of claim 1, wherein the smartphone interface comprises a frame configured to couple to the second end of the tubular body to form the camera opening, wherein the base projection is integral with or coupled to the frame.

5. The system of claim 1, wherein the tubular body comprises a diffusive material configured to diffuse light within the central lumen.

6. The system of claim 1, wherein the tubular body is tapered from the first end to the second end.

7. The system of claim 1, wherein the tubular body extends between 70 mm and 95 mm in length.

8. The system of claim 1, wherein the rim of the patient interface extends proud of the tubular body.

9. The system of claim 1, wherein the patient interface forms an opening into the central lumen that is between 50 mm and 70 mm long.

10. The system of claim 9, wherein the opening into the central lumen is between 35 mm and 50 mm wide.

11. The system of claim 1, wherein the smartphone interface comprises a gasket around the second end to prevent light from entering the central lumen between the smartphone and the second end.

12. The system of claim 1, wherein the base projection comprises a plurality of openings configured to engage with the array of projecting members.

13. The system of claim 1, wherein the clip or clamp comprises a clamp formed by two or more pieces configured to be secured together to apply compression to the smartphone.

14. The system of claim 1, wherein the rim of the patient interface is a rounded rim extending between 3 mm and 10 mm at least partially around the circumference of the first end of the tubular body.

15. A system, the system comprising:
a tubular body having a central lumen extending therethrough, from a first end to a second end;
a patient interface on the first end of the tubular body, having a rim configured to fit between a patient's lips and gums; and
a smartphone interface at the second end of the tubular body, wherein the smartphone interface comprises:
an annular base region forming an opening into the central lumen that is configured to fit over one or more cameras of a smartphone; and a base projection extending parallel to the annular base region and laterally offset from the annular base region and one or more openings disposed on the base projection; and a securement configured to clamp or clip to one or more sides of the smartphone, wherein the securement comprises an array of projecting members, wherein the one or more openings of the base projection are configured to attach to and detach from the securement through a subset of the array of projecting members and one or more openings within the base projection, and wherein the securement is configured to retain the smartphone at a location corresponding to a position at which the base projection is attached to the securement, wherein the annular base region is configured to cantilever over a back of the smartphone when the base projection is held against the back of the smartphone by the securement.

16. The system of claim 15, wherein the tubular body comprises a diffusive material configured to diffuse light within the central lumen.

17. The system of claim 15, wherein the rim of the patient interface comprises a pair of sections on opposite sides of the first end of the tubular body that flare outwards to form a saddle shaped mouth region.

18. The system of claim 15, wherein the smartphone interface includes a frame configured to couple to the second end of the tubular body to form a camera opening, wherein the base projection is integral with or coupled to the frame.

19. The system of claim 15, wherein the tubular body is tapered from the first end to the second end.

20. The system of claim 15, wherein the patient interface forms an opening into the central lumen that is between 50 mm and 70 mm long.

21. The system of claim 15, wherein the smartphone interface comprises a gasket configured to prevent light from entering the central lumen between the smartphone and the second end of the tubular body.

22. The system of claim 15, wherein the base projection comprises a plurality of openings configured to engage with the array of projecting members.

23. The system of claim 15, wherein the securement comprises a clamp formed by two or more pieces configured to be secured together to apply compression to the smartphone.

* * * * *